United States Patent [19]

Deutsch et al.

[11] Patent Number: 5,693,309

[45] Date of Patent: *Dec. 2, 1997

[54] SUBSTITUTED COMPLEXING AGENTS, COMPLEXES, AND COMPLEX SALTS, PROCESSES FOR THEIR PRODUCTION, AND PHARMACEUTICALS CONTAINING SAME

[75] Inventors: Julius Deutsch; Heinz Gries; Erich Klieger; Ulrich Niedballa, all of Berlin; Franz-Josef Renneke, Bergkamen; Jürgen Conrad, Berlin; Wolfgang Muetzel, Berlin; Heribert Schmitt-Willich, Berlin, all of Germany

[73] Assignee: Schering Aktiengesellschaft, Berlin, Germany

[*] Notice: The term of this patent shall not extend beyond the expiration date of Pat. No. 5,482,700.

[21] Appl. No.: 462,213

[22] Filed: Jun. 5, 1995

Related U.S. Application Data

[63] Continuation-in-part of Ser. No. 269,504, Jul. 1, 1994, Pat. No. 5,482,700, which is a continuation of Ser. No. 66,646, May 25, 1993, abandoned, which is a continuation of Ser. No. 715,713, Jun. 18, 1991, abandoned, which is a continuation of Ser. No. 430,442, filed as PCT/DE88/00199, Mar. 28, 1988, abandoned.

[30] Foreign Application Priority Data

Mar. 31, 1987 [DE] Germany ............................ 37 10 730.5

[51] Int. Cl.⁶ .......................... A61B 5/055; A61K 49/04
[52] U.S. Cl. .................... 424/9.364; 424/9.42; 514/492; 514/502; 514/836; 534/16; 556/50; 556/55; 556/63; 556/77; 556/90; 556/105; 556/116; 556/134; 556/148; 436/173
[58] Field of Search ................... 424/9.364, 9.42; 514/492, 502, 836; 534/16; 556/50, 55, 63, 77, 90, 105, 116, 134, 148; 436/173; 128/653.4, 654

[56] References Cited

U.S. PATENT DOCUMENTS

| | | | |
|---|---|---|---|
| 3,364,165 | 1/1968 | Zimmermann | 260/29.7 |
| 3,994,966 | 11/1976 | Sundberg | 260/581 R |
| 4,339,426 | 7/1982 | Meares | 424/1 |
| 4,622,420 | 11/1986 | Meares | 562/443 |
| 4,647,447 | 3/1987 | Gries | 424/9 |
| 4,652,519 | 3/1987 | Warshawsky | 435/7 |

FOREIGN PATENT DOCUMENTS

| | | |
|---|---|---|
| 0 165 716 | 11/1985 | European Pat. Off. . |
| 0 178 125 | 4/1986 | European Pat. Off. . |
| 21 63 601 | 6/1972 | Germany . |
| 34 01 052 | 7/1984 | Germany . |
| 1374979 | 1/1974 | United Kingdom . |
| 2137612 | 10/1984 | United Kingdom . |

OTHER PUBLICATIONS

Stetter et al., Tetrahedron, 37:767–772 (1981). Month not available.

Kostial, Arh. Hig. Rada., 18:111–123 (1967). Month not available.

Lauterbur, Stereodynamics of Molecular Systems, Ed. Sarma, Pergamon Press, Oxford, pp. 453–456 (1979). Month not available.

Carr, J. Am. Chem. Soc., 97(2):315–321 (1975). Month not available.

Sudmeier et al., Analytical Chemistry, 40(11):1693–1698 (Sep. 1968).

Bailey et al., J. of Chromatography, 25:442–446 (1966). Month not available.

Chemical Abstracts, 105:232452p (1986). Month not available.

Chemical Abstracts, 105(7):57095a (Aug. 18, 1986).
Chemical Abstracts, 98(15):120828w (Apr. 11, 1983).
Chemical Abstracts, 99(23):19440t (Dec. 5, 1983).
Chemical Abstracts, 71(5):25207b (Aug. 4, 1969).
Chemical Abstracts, 73(19):98343u (Nov. 9, 1970).
Chemical Abstracts, 70(13):57167j (Mar. 31, 1969).
Chemical Abstracts, 93(21):197550d (Nov. 24, 1980).
Chemical Abstracts, 74(13):61428v (Mar. 29, 1971).

*Primary Examiner*—Gary E. Hollinden
*Attorney, Agent, or Firm*—Millen, White, Zelano & Branigan, P.C.

[57] ABSTRACT

1. Compounds of general Formula I

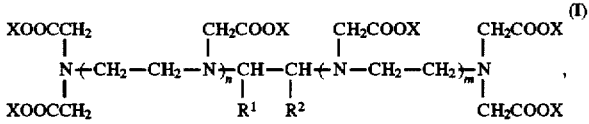

wherein n and m in each case mean the numbers 0, 1, 2, 3 and 4, X stands for a hydrogen atom and/or a metal ion equivalent of an element of atomic numbers 21–29, 31, 32, 37–39, 42–44, 49 or 57–83, $R^1$ and $R^2$, being different, mean in each case a hydrogen atom or a straight-chain, branched, saturated or unsaturated $C_0$–$C_{20}$-alkylene group, this alkylene group exhibiting at the end either a second molecule of general Formula $I_A$ or $I_B$

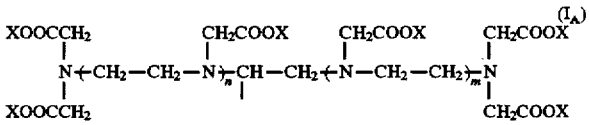

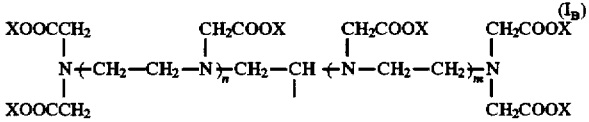

a functional group, or, linked by way of this functional group, a bio- or macromolecule, are valuable diagnostic and therapeutic media,

28 Claims, No Drawings

SUBSTITUTED COMPLEXING AGENTS, COMPLEXES, AND COMPLEX SALTS, PROCESSES FOR THEIR PRODUCTION, AND PHARMACEUTICALS CONTAINING SAME

CROSS-REFERENCE TO RELATED APPLICATIONS

This application is a continuation-in-part of application Ser No. 08/269,504, filed Jul. 1, 1994 now U.S. Pat. No. 5,482,700, hereby incorporated in its entirety, which is a continuation of Ser. No. 08/066,646, filed May 25, 1993 (abandoned), which is a continuation of Ser. No. 07/715,713, filed Jun. 18, 1991 (abandoned), which is a continuation of Ser. No. 07/430,442, filed Oct. 2, 1989 (abandoned), which is based on international application PCT/DE88/00199, filed Mar. 28, 1988.

The invention relates to the subject matter characterized in the claims, i.e., novel complexing agents, complexes, and complex salts, media containing these compounds, their use in diagnostics and therapy, as well as processes for the production of these compounds and media.

The use of complexing agents or complexes and, respectively, their salts in medicine has been known for a long time. The following examples can be cited:

Complexing agents as stabilizers for pharmaceutical preparations, complexes and their salts as auxiliary media for administration of poorly soluble ions (e.g., iron), complexing agents and complexes (preferably calcium or zinc compounds), optionally in the form of salts with inorganic and/or organic bases, as antidotes for detoxification in case of inadvertent ingestion of heavy metals, or their radioactive isotopes and complexing agents as auxiliary media in nuclear medicine using radioactive isotopes, such as $^{99m}$Tc for scintigraphy, all have been known. Recently, patent publication DOS 3,401,052 has suggested paramagnetic complex salts as diagnostic media, predominantly as NMR diagnostic media.

All of the heretofore known complexes and their salts cause problems in their clinical usage with respect to compatibility and/or selectivity of binding and/or stability. These problems become the more pronounced, the higher the dosages that must be utilized for the products derived from the complexing agents. Use of heavy elements, inherently beneficial, as components of X-ray contrast media to be administered parenterally has failed thus far due to inadequate compatibility of such compounds. In the paramagnetic materials heretofore proposed or tested for NMR tomography, the interval between the effective dose and the dose toxic in animal experiments is relatively narrow and/or the materials show low organ specificity and/or stability and/or contrast-enhancing effect and/or their compatibility is insufficient.

Only very limited success has been achieved thus far in attempting to solve at least part of these problems by the use of complexing agents bound, on the one hand, by ionic linkage to the respectively suitable metal (see below) as well as, on the other hand, by linkage to a functional group or to a macromolecule that is nontoxic and maximally organ-specific and serves as the carrier molecule.

When utilizing the functional groups of the complexing agent for linking the molecule to a bio-molecule, then complex stability is weakened, i.e. a physiologically intolerable proportion of the metal ions of the macromolecule-metal ion complex is liberated [C. H. Paik et al., J. Radioanal. Chem. 57: 553 (1980); D. J. Hnatowich et al., J. Nucl. Med. 26: 503 (1985)].

On the other hand, when using as the educts bifunctional complexing agents, i.e. complexing compounds carrying functional groups for coordinative linkage of the desired metal ion as well as a (different) functional group for binding the macromolecule, then a great variety of grave disadvantages occur according to the present state of the art (C. F. Meares et al., Radioimmunoimaging and Radioimmunotherapy 1983: 185; Canadian Patent No. 1,178,951): There are, for example, low stability of the complexes, multistage, difficult synthesis of the complexes, small variation possibilities of the functional group required for binding to the macromolecule, danger of contamination of the complexing agents during their synthesis with foreign metals, only limited reaction possibilities of the complexing agents on account of a lipophily that is too low, required intermediate blockage of the functional groups of the complexing agents (e.g. as iron complex or blockage of a phenolic hydroxy group as the methyl ether) accompanied by a reduction in yield and additional purification steps, necessity of having to work with highly purified solvents and apparatuses.

Therefore, there is a need, for variegated purposes, for stable, readily soluble and adequately selective, but also more compatible, easily accessible complex compounds exhibiting a maximum variety of functional groups suitable for linkage to macromolecules. Therefore, the invention is based on the object of making these compounds and media available as well as of providing a maximally simple process for their production. This object has been attained by the invention.

It has been found that compounds consisting of the anion of a monofunctionalized aminopolycarboxylic acid and one or several central ions of an element of atomic numbers 21–29, 31, 32, 37–39, 42–44, or 57–83, as well as optionally one or several cations of an inorganic and/or organic base or amino acid are surprisingly excellently suitable for the production of NMR, X-ray and radiodiagnostic media, as well as radio-therapeutic media.

The compounds according to this invention are described by general Formula I

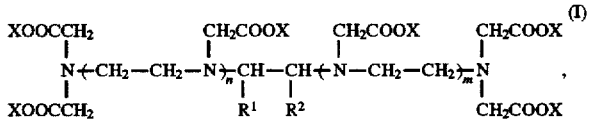

wherein n and m in each case mean the numbers 0, 1, 2, 3 and 4,

X stands for a hydrogen atom and/or a metal ion equivalent of an element of atomic numbers 21–29, 31, 32, 37–39, 42–44, 49 or 57–83, $R^1$ and $R^2$ being different mean in each case a hydrogen atom or a straight-chain, branched, saturated or unsaturated $C_0$–$C_{20}$-alkylene group which optionally contains imino, phenylenoxy, phenylenimino, amido, hydrazido, ester group(s), oxygen, sulfur and/or nitrogen atom(s) and is substituted, if desired, by hydroxy, mercapto, imino, epoxy, oxo, thioxo and/or amino group(s), this alkylene group exhibiting at the end either a second molecule of general Formula $I_A$ or $I_B$

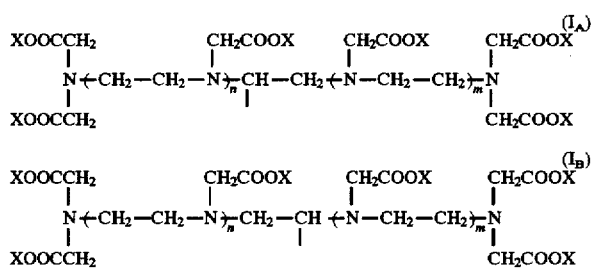

a functional group, or, linked by way of this functional group, a bio- or macromolecule, with the proviso that n and m jointly do not result in more than 4 and that, if X means a metal ion equivalent, at least two of the substituents X have this meaning.

Compounds of general Formula I wherein X means hydrogen are denoted as complexing agents and, with at least two of the substituents X meaning a metal ion equivalent, are denoted as metal complexes.

The element of the above-mentioned atomic number constituting the central ion of the physiologically compatible complex salt can, of course, also be radioactive for the intended utilization of the diagnostic medium according to this invention.

If the medium of this invention is meant for NMR diagnostics, then the central ion of the complex salt must be paramagnetic. This means, in particular, the divalent and trivalent ions of the elements of atomic numbers 21–29, 42, 44, and 58–70. Suitable ions are, for example, the chromium (III), manganese(II), iron(II), cobalt(II), nickel(II), copper (II), praseodymium(III), neodymium(III), samarium(III) and ytterbium(III) ions. On account of their very strong magnetic moment, especially preferred are gadolinium(III), terbium(III), dysprosium(III), holmium(III), erbium(III) and iron(III) ions.

For using the media of this invention in nuclear-medicine diagnostics, the central ion must be radioactive. Suitable are, for example, radioisotopes of the elements copper, cobalt, gallium, germanium, yttrium, strontium, technetium, indium, gadolinium, samarium and iridium.

For use of the media according to this invention in nuclear medicine, the central ion must be radio-active. Suitable are, for instance, radioisotopes of the elements copper, cobalt, gallium, germanium, yttrium, strontium, technetium, indium, ytterbium, gadolinium, samarium and iridium.

If the medium of this invention is intended for use in X-ray diagnostics, then the central ion must be derived from an element of a higher atomic number in order to achieve adequate absorption of the X-rays. It has been found that this requirement is met by diagnostic media containing a physiologically compatible complex salt with central ions of elements of atomic numbers of between 21 and 29, 42, 44, 57–83; these are, for example, the lanthanum(III) ion and the above-cited ions of the lanthanide series.

The alkylene group contained in $R^1$ and $R^2$, respectively, can be straight-chain, branched, cyclic, aliphatic, aromatic or arylaliphatic and can contain up to 20 carbon atoms. Preferred are straight-chain mono- to hexamethylene groups as well as $C_1$–$C_4$-alkylenephenyl groups. In case the alkylene group contains a phenoxy group, the latter is linked preferably in the p-position via a methylene group to the —CH-group of the basic skeleton of the compound according to general Formula I.

Preferred functional groups present at the end of the $R^1$ and, respectively, $R^2$ alkylene group are, for example, the benzyl ester, ethyl ester, tert-butyl ester, amino, $C_1$–$C_6$-alkylamino, aminocarbonyl, hydrazino, hydrazinocarbonyl, maleimido, methacrylamido, methacryloylhydrazinocarbonyl, maleimidamidocarbonyl, halo, mercapto, hydrazinotrimethylenehydrazinocarbonyl, aminodimethylenamidocarbonyl, bromocarbonyl, phenylenediazonium, isothiocyanate, semicarbazide, thiosemicarbazide groups.

For explanatory purposes, several selected $R^1$ and, respectively, $R^2$ substituents are listed below:

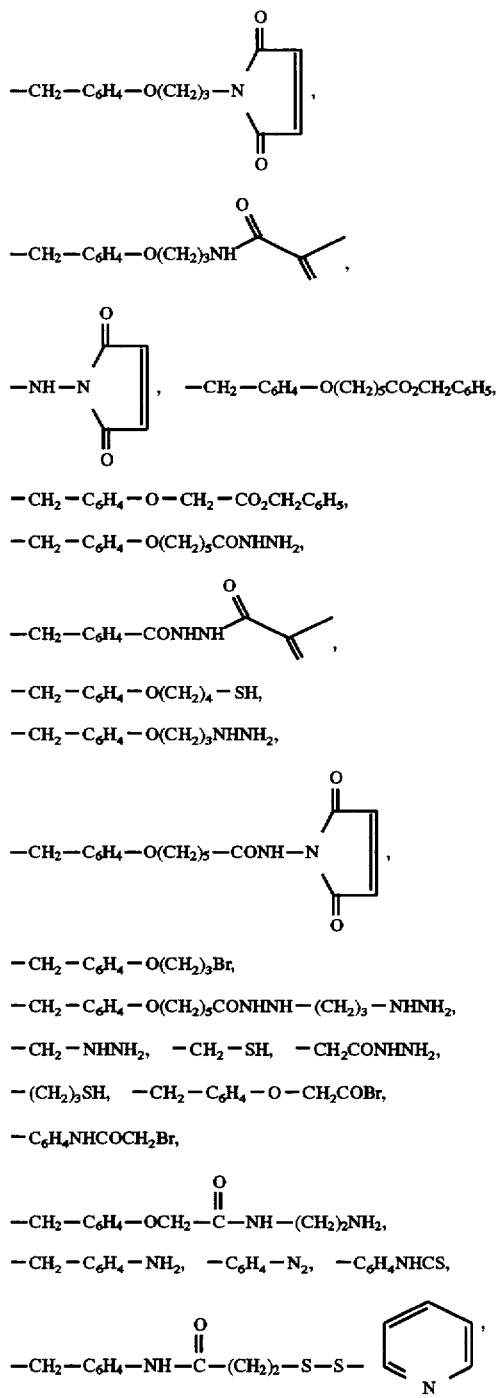

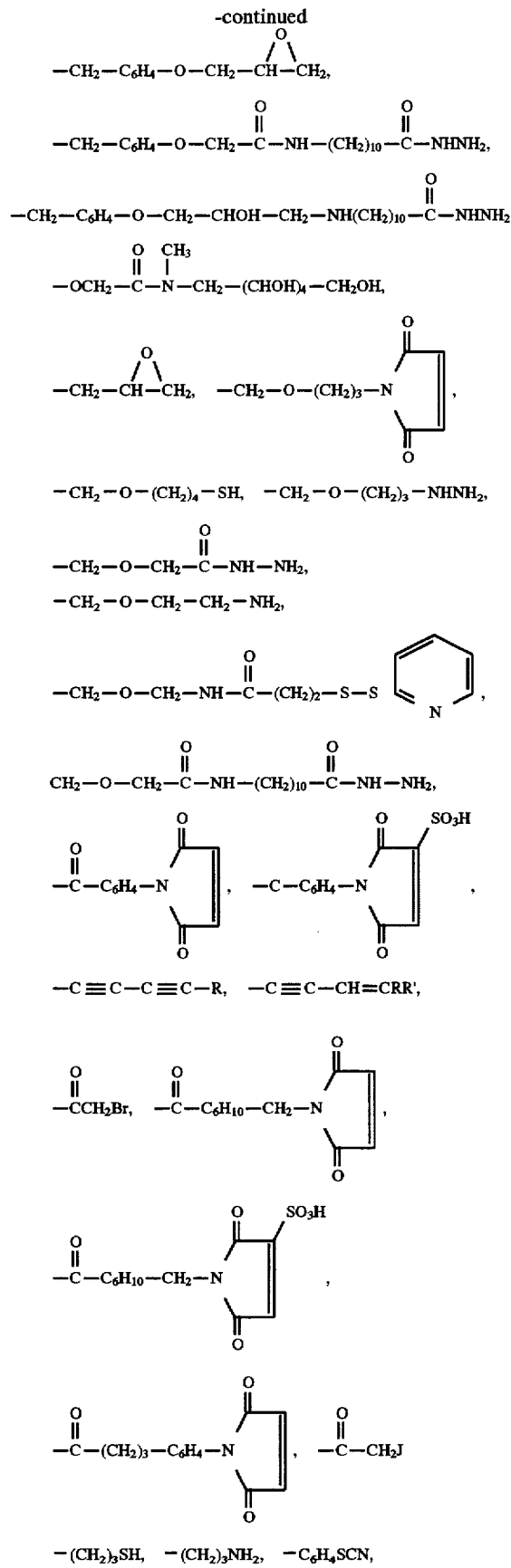

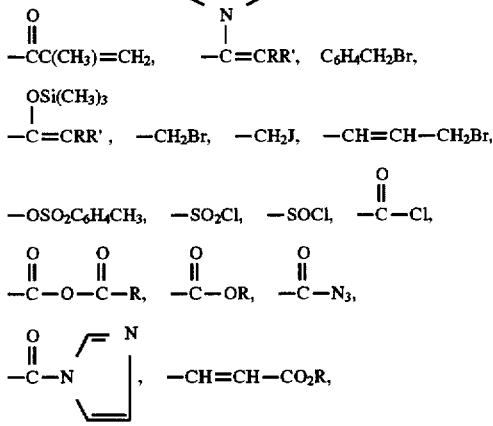

wherein
R and R' being identical or different, mean respectively a hydrogen atom, a saturated or unsaturated $C_1$–$C_{20}$-alkyl residue optionally substituted by a phenyl group, or a phenyl group.

In case not all of the acidic hydrogen atoms are substituted by the central ion, it is possible to replace one, several or all of the remaining hydrogen atom(s) by cations of inorganic and/or organic bases or amino acids. Suitable inorganic cations are, for example, the lithium ion, the potassium ion, the calcium ion and, in particular, the sodium ion. Suitable cations of organic bases are, inter alia, those of primary, secondary or tertiary amines, e.g. ethanolamine, diethanolamine, morpholine, glucamine, N,N-dimethylglucamine and especially N-methylglucamine. Suitable cations of amino acids are, for example, those of lysine, of arginine and of ornithine.

The complexing agents according to this invention are produced by saponifying compounds of general Formula II

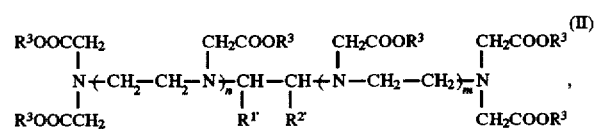

wherein n and m have the meanings given above, $R^{1'}$ and $R^{2'}$ are different and in each case mean a hydrogen atom or a straight-chain, branched, saturated or unsaturated $C_0$–$C_{20}$-alkylene group optionally containing imino, phenylenoxy, phenylenimino, amido, hydrazido, ester group(s), oxygen, sulfur and/or nitrogen atom(s) and, if desired, substituted by hydroxy, mercapto, imino, epoxy, oxo, thioxo and/or amino group(s), this alkylene group exhibiting at the end a second molecule of general Formula $\Gamma_A$ or $\Gamma_B$

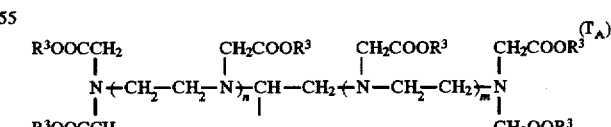

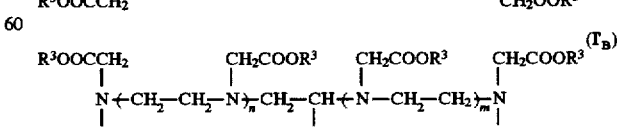

or a functional group,
and $R^3$ means a $C_1$–$C_6$-alkyl residue.

Saponification is conducted according to the methods known to persons skilled in the art, for example, in case of tert-butyl esters, with the aid of trifluoroacetic acid.

The educts are prepared by alkylation of monosubstituted polyamines of general Formula III

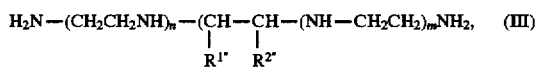

wherein n and m each stands for the numbers 0, 1, 2, 3 and 4, and $R^{1''}$ and $R^{2''}$ respectively mean a hydrogen atom or a substituent which can be converted into $R^{1'}$ and $R^{2'}$, respectively, with the proviso that n and m jointly are no more than 4, that the substituents $R^{1''}$ and $R^{2''}$ are different and one stands for a hydrogen atom and the other for a substituent convertible into $R^{1'}$ and $R^{2'}$ respectively, with an ester of general Formula IV

wherein Hal means chorine, bromine or iodine and $R^3$ has the meanings given for general Formula II.

The reaction takes place in polar aprotic solvents, such as, for example, dimethylformamide, dimethyl sulfoxide or hexamethylphosphoric triamide in the presence of an acid neutralizer, e.g. tertiary amine (e.g. triethylamine, trimethylamine, N,N-dimethylaminopyridine, 1,5-diazabicyclo[4.3.0]nonene-5 [DBN], 1,5-diazabicyclo [5.4.0]undecene-5), alkali, alkaline earth carbonate or bicarbonate (for example, sodium, magnesium, calcium, barium, potassium carbonate and bicarbonate) at temperatures of between −10° C. and 120° C., preferably between 0° C. and 50° C.

Methods known from the literature are employed for the synthesis of dimers, i.e. compounds of general Formula I wherein the $C_0$–$C_{20}$-alkylene group contained in $R^1$ and $R^2$ is bound to a second molecule of general Formula $I_A$ or $I_B$, for example by way of an addition/elimination reaction of an amine with a carbonyl compound (e.g. acid chloride, mixed anhydride, activated ester, aldehyde); of two amine-substituted rings with a dicarbonyl compound (for example oxalyl chloride, glutaric dialdehyde); of two rings each exhibiting a nucleophilic group, with an alkylene compound carrying two leaving groups or, in case of terminal acetyls, by oxidative coupling (Cadiot, Chodkiewicz in Viehe "Acetylenes", 597–647, Marcel Dekker, New York, 1969).

The chain linking the two halves of the molecule can subsequently be modified by follow-up reactions (e.g. hydrogenation).

Suitable substituents $R^{1''}$ and $R^{2''}$, respectively, are, inter alia, hydroxy and nitrobenzyl, hydroxy and carboxyalkyl, as well as thioalkyl residues of up to 10 carbon atoms. They are converted by means of methods of the literature known to those skilled in the art [Chem.-Pharm. Bull. 33: 674 (1985), Compendium of Org. Synthesis, vol. 1–5, Wiley and Sons, Inc.] into the desired substituents (e.g. with the amino, hydrazino, hydrazinocarbonyl, methacryloylhydrazinocarbonyl, maleimidamidocarbonyl, halo, halocarbonyl, mercapto group as the functional group) wherein, in case of the nitrobenzyl residue, a catalytic hydrogenation must first be performed to the aminobenzyl derivative (for example in accordance with P. N. Rylander, Catalytic Hydrogenation Over Platinum Metals, Academic Press 1967).

Examples for the conversion of hydroxy or amino groups linked to aromatic or aliphatic residues are the reactions, performed in anhydrous, aprotic solvents such as tetrahydrofuran, dimethoxyethane or dimethyl sulfoxide in the presence of an acid neutralizer, such as, for example, sodium hydroxide, sodium hydride or alkali or alkaline earth carbonates, such as, for example, sodium, magnesium, potassium, calcium carbonate, at temperatures of between 0° C. and the boiling point of the respective solvent, but preferably between 20° C. and 60° C., with a substrate of general Formula V

wherein Z is a nucleofugal entity, such as, for example, Cl, Br, I, $CH_3C_6H_4SO_3$ or $CF_3SO_3$, L is an aliphatic, aromatic, arylaliphatic, branched, straight-chain or cyclic hydrocarbon residue of up to 20 carbon atoms, and Fu means the desired end-positioned functional group, optionally in blocked form (DOS 3,417,413).

Examples that can be cited for compounds of general Formula V are

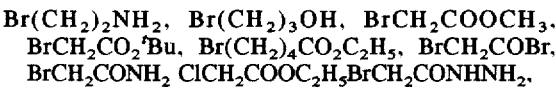

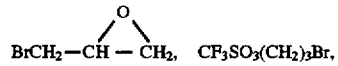

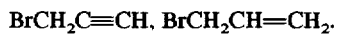

Conversions of carboxy groups can be performed, for example, according to the carbodiimide method (Fieser, Reagents for Organic Syntheses, 10: 142) via a mixed anhydride [Org. Prep. Proc. Int. 7: 215 (1975)] or via an activated ester (Adv. Org. Chem. Part B, 472).

The amines of general Formula III required as the starting compounds are prepared analogously to methods known from the literature (for example, Canad. Patent No. 1,178, 951, Eur. I. Med. Chem.-Chim. Ther. 1985, 20: 509, and 1986, 21: 333) by starting with amino acids which are converted into amides that are optionally substituted with ethylenamine [e.g. with N-(2-aminoethyl)carbamic acid benzyl ester] and then are reduced to the desired amines (preferably with diborane or lithium aluminum hydride).

If compounds are to be synthetized according to general Formula I where $R^1$ means a hydrogen atom, then it is necessary to substitute such an amide prior to reduction on the α-amino group by reacting with, for example, ethyl oxamate in a polar solvent, e.g. tetrahdyrofuran, dimethyl sulfoxide or dimethoxyethane, at a temperature of between 50° C. and 250° C., preferably 70° C. to 150° C. (optionally in a pressurized vessel) so that a 3-aza-2-oxoglutaric acid diamide derivative is obtained as the intermediate.

The resultant complex-forming ligands (as well as the complexes) can also be linked to bio- or macromolecules of which it is known that they are especially enriched in the organ or organ part to be investigated. Such molecules are, for example, enzymes, hormones, sugars, dextrans, lectins, porphyrins, bleomycins, insulin, prostaglandins, steroid hormones, amino sugars, amino acids, peptides, such as polylysine, proteins (e.g. immunoglobulins and monoclonal antibodies) or lipids (also in the form of liposomes). Conjugates with albumins, such as human serum albumin, antibodies, such as, for example, monoclonal antibodies specific for tumor-associated antigens, antimyosin or cholic acid can be emphasized, in particular. Instead of biomolecules, it is also possible to link suitable synthetic polymers, such as polyethylenimines, polyamides, polyureas, polyethers and polythioureas. The resultant pharmaceutical agents are suited, for example, for use in tumor and infarction diagnostics, as well as in tumor therapy. Suitable monoclonal antibodies (e.g. Nature 256: 495, 1975), having the advantages over the polyclonal antibodies of being specific for an antigen determinant, exhibiting defined binding affinity, being homogeneous (thus substantially facilitating their production in pure form), and being producible in cell cultures in large amounts, are especially those for the conjugation which are directed against predominantly cell-membrane-located antigens. Suitable as those are, for example, for tumor imaging monoclonal antibodies and/or their fragments Fab and F(ab')$_2$ which are specific, for example, for human tumors of the gastrointestinal tract, of the breast, the liver, the bladder, the reproductive glands, and of melanomas (Cancer Treatment Repts. 68: 317, 1984, Bio. Sci. 34: 150, 1984) or against Carcinoembryonales Antigen (CEA), Humanes Choriogonadotropin ($\beta$-HCG), or other tumor-located antigens, such as glycoproteins (New Engl. J. Med. 298: 1384, 1973, U.S. Pat. No. 4,331,647). Likewise suitable are, inter alia, anti-myosin, anti-insulin and anti-fibrin antibodies (U.S. Pat. No. 4,036, 945).

Suited for liver tests and gallbladder-diagnostics or tumor diagnostics are the monomeric complexes as well as conjugates or clathrates with liposomes (used, for example, as unilamellar or multi-lamellar phosphatidyl choline cholesterol vesicles).

The linkages known from the state of the art of, for example, radioisotopes to immunoglobulins and their fragments suffer from the disadvantage of lack of stability of the labeled antibody conjugates and/or lack of specificity (for example on account of the use of a diethylenetriaminepentaacetic acid=DTPA anhydride)(for example, Diagnostic Imaging 84: 56; Science 220: 613, 1983; Cancer Drug Delivery 1: 125, 1984).

In contrast thereto, the formation of the conjugate in accordance with the present invention takes place by way of the functional group located at the end of the $C_0$–$C_{20}$-alkylene group of substituent $R^1$ or $R^2$, as defined hereinabove. In the conjugate formation of the acids with bio- or macromolecules, several acid residues can be bound to the latter. In this case, each acid residue can carry a central ion.

Coupling to the desired macromolecules likewise takes place according to methods known per se, as described, for example, in Rev. Roum. Morphol. Embryol. Physio., Physiologie 1981, 18: 241 and J. Pharm. Sci. 68: 79 (1979), for example by reacting the nucleophilic group of a macromolecule, such as the amino, phenol, sulfhydryl, aldehyde or imidazole group, with an activated derivative of the complexing agent. Examples of suitable activated derivatives are mono-anhydrides, acid chlorides, acid hydrazides, mixed anhydrides (see, for example, G. E. Krejcarek and K. L. Tucker, Biochem., Biophys. Res. Commun. 1977: 581), activated esters, nitrenes or isothiocyanates. Conversely, it is also possible to react an activated macromolecule with the complexing acid. For the conjugation with proteins, likewise suitable are substituents having, for example, the structure $C_6H_4N_2$, $C_6H_4NHCOCH_2$, $C_6H_4NHCS$ or $C_6H_4OCH_2CO$.

In case of the antibody conjugates, the linkage of the antibody to the complexing agent (or to the metal complex; production of the metal complex conjugate can take place in the sequence of complexing agent, complexing agent-conjugate, final product, as well as in the sequence complexing agent, metal complex, final product) must not lead to loss or reduction of binding affinity and binding specificity of the antibody to the antigen. This can be accomplished either by linkage to the carbohydrate portion in the Fc part of the glycoprotein or, respectively, in the Fab or F(ab')$_2$fragments; or by linkage to sulfur atoms of the antibody or of the antibody fragments.

In the former case, an oxidative splitting of sugar units must first be carried out to generate formyl groups capable of coupling. This oxidation can take place by chemical methods with oxidizing agents such as, for example, periodic acid, sodium metaperiodate or potassium metaperiodate in accordnace with processes known from the literature (e.g. J. Histochem. and Cytochem. 22: 1084, 1974) in an aqueous solution in concentrations of 1–100, preferably 1–20 mg/ml, and with a concentration of the oxidizing agent of between 0.001 and 10 millimoles, preferably 1–10 mmol, in a pH range of about 4–8 at a temperature of between 0° and 37° C. and with a reaction period of between 15 minutes and 24 hours. The oxidation can also be performed by an enzymatic method, for example with the aid of galactose oxidase in an enzyme concentration of 10–100 units/ml, a substrate concentration of 1–20 mg/ml, at a pH of 5–8, a reaction time of 1–8 hours, and at a temperature of between 20° and 40° C. (for example J. Biol. Chem. 234: 445, 1959).

Complexing agents (or metal complexes, see above) with suitable functional groups, e.g. hydrazine, hydrazide, primary amine, hydroxylamine, phenyl-hydrazine, semicarbazide and thiosemicarbazide are linked to the aldehydes generated by oxidation, by reaction at between 0° and 37° C., with a reaction period of 1–65 hours, a pH of between about 5.5 and 8, an antibody concentration of 0.5–20 mg/ml, and a molar ratio of the complexing agent to the antibody aldehyde of 1:1 to 1000:1. The subsequent stabilization of the conjugate takes place by reduction of the double bond, for example with sodium borohydride or sodium cyanoborohydride; the reducing agent is utilized in this process in a 10- to 100-fold excess (for example, J. Biol. Chem. 254: 4359, 1979).

The second possibility of forming antibody conjugates starts with a gentle reduction of the disulfide bridges of the immunoglobulin molecule; in this step, the more sensitive disulfide bridges of the H-chains of the antibody molecule are cleaved while the S-S-linkages of the antigen-binding region remain intact so that there is practically no diminution of the binding affinity and specificity of the antibody (Biochem. 18: 2226, 1979, Handbook of Experimental Immunology, vol. 1, Second Edition, Blackwell Scientific Publications, Lindon 1973, chapter 10). These free sulfhydryl groups of the intra-H-chain regions are then reacted with suitable functional groups of complexing agents or metal complexes at 0°–37° C., a pH of about 4–7, and a reaction time of 3–72 hours with the formation of a covalent bond not affecting the antigen binding region of the antibody. Examples of suitable reactive groups are: haloalkyl, haloacetyl, p-mercuribenzoate groups, as well as groups to be subjected to a Michael addition reaction, such as, for example, maleinimides, methacrylo groups (for example J. Amer. Chem. Soc. 101: 3097, 1979).

It is also possible to utilize linkages of a non-covalent type for coupling purposes; in this connection, ionic as well as van der Waals and hydrogen bridge linkages can contribute toward the linking step in varying proportions and intensity (lock-and-key principle)(for example, avidin-biotin, antibody-antigen). Also clathrate compounds (host-guest) of relatively small complexes in relatively large cavities in the macromolecule are possible.

The coupling principle resides in initially producing a bifunctional macromolecule either by fusing an antibody hybridoma directed against a tumor antigen with a second antibody hybridoma directed against a complex according to this invention, or by linking the two antibodies with each other chemically via a linking agent [for example in the manner disclosed in J. Amer. Chem. Soc. 101: 3097 (1979)] or binding the antibody directed against the tumor antigen to avidin (or biotin), if needed, by way of a linking agent [D. J. Hnatowich et al., J. Nucl. Med. 28: 1294 (1987)]. Instead of the antibodies, it is also possible to use their corresponding F(ab) or F(ab')$_2$ fragments. For pharmaceutical usage, the bifunctional macromolecule is injected first of all, this molecule accumulating at the target site, and then, at a time interval, the complex compound [optionally bound to biotin (or avidin)] is injected which is coupled in vivo at the target site and can there deploy its diagnostic or therapeutic effect. Moreover, other coupling methods can likewise employed, such as, for example, "reversible radiolabeling" described in Protein Tailoring Food Med. Uses [Am. Chem. Soc. Symp.] (1985), 349.

A method especially well suited for the production of conjugates of antibodies as well as antibody fragments is the coupling to a solid phase. In this process, the antibody or the corresponding F(ab)$_2$ fragment is bound to a stationary phase (e.g. an ion exchanger) located in a column equipped with inlet and outlet and being temperature-controllable. For the oxidation in the Fc portion of the antibody, the column must be protected from the effect of light by providing coverage; for the reduction of disulfide bridges (for example in the generation of Fab fragments) the process must be performable under argon as a protective gas. The actual coupling step then takes place as follows:

After flushing of the column with a suitable buffer, a solution is used as the eluent which produces reactive groups on the bound protein (for example, periodate solution for the production of aldehyde groups in the Fc portion of monoclonal antibodies or mercaptoethylamine solution for the production of sulfhydryl groups in fragments). After the reaction solution has completely displaced the previous eluent, throughflow is stopped for a time adequate for complete reaction, then adequate flushing is carried out with a buffer, whereafter a solution with the coupling partner (e.g. the hydrazide or dithiopyridyl derivative of a complexing agent or of a complex) is applied, and throughflow is once more stopped for an adequate time length. Instead of stopping throughflow for a relatively long period of time, it is also possible to use a so-called recycle circuit; in this process, the eluate leaving the column is directly pumped back into the column by means of a loop circuit. In this method, on account of improved intermixing, substantially shorter reaction times and higher yields are obtained. Thereafter, flushing is again performed with buffer solution. If a free complexing agent is the coupling partner, then, in a further cycle, complexing is conducted with a solution of the desired metal salt (for example a citrate solution) as well as a subsequent flushing step. Finally, the conjugate is eluted with a pH gradient or salt gradient. Subsequently, a lyophilizing step is carried out, optionally after desalting. After equilibration with buffer solution, the column is ready for the next coupling step.

This method, for the production of very small as well as very large quantities of conjugate, is far superior to the conventional methods with respect to speed and also yield, and permits also the continuous preparation of conjugates; this is the prerequisite for an economical production of relatively large amounts.

The thus-formed compounds are subsequently purified preferably by chromatography via ion exchangers on a fast protein liquid chromatography facility.

The thus-obtained compounds of general Formula I wherein X means a hydrogen atom represent complex-forming agents. They can be isolated and purified, or they can be converted without isolation into metal complexes of general Formula I with at least two of the substituents X meaning a metal ion equivalent.

The metal complexes of this invention are produced as disclosed in the patent publication DOS 3,401,052, by dissolving or suspending the metal oxide or a metal salt (e.g. the nitrate, acetate, carbonate, chloride or sulfate) of the element of atomic numbers 21–29, 31, 32, 38, 39, 42–44, 49, 57–83, in water and/or in a lower alcohol (such as methanol, ethanol or isopropanol) and reacting with a solution or suspension of the equivalent amount of the complexing acid of general Formula I wherein X means a hydrogen atom, and subsequently, if desired, substituting any acidic hydrogen atoms of acid groups that may be present by cations of inorganic and/or organic bases or amino acids.

Neutralization takes place in this process with the aid of inorganic bases (for example hydroxides, carbonates or bicarbonates) of, for example, sodium, potassium or lithium and/or of organic bases, such as, inter alia, primary, secondary and tertiary amines, e.g. ethanolamine, morpholine, glucamine, N-methyl- and N,N-dimethylglucamine, as well as alkaline amino acids, e.g. lysine, arginine and ornithine.

For producing the neutral complex compounds, such an amount of the desired bases can, for example, be added to the acidic complex salts in an aqueous solution or suspension that the neutral point is attained. The thus-produced solution can then be evaporated to dryness under vacuum. It is frequently advantageous to precipitate the thus-formed neutral salts by adding water-miscible solvents, such as, for example, lower alcohols (methanol, ethanol, isopropanol and others), lower ketones (acetone and others), polar ethers (tetrahydrofuran, dioxane, 1,2-dimethoxyethane and others), thus obtaining crystallized products that can be readily isolated and are easily purified. It proved to be especially advantageous to add the desired base as early as during the complex formation to the reaction mixture and thereby to save a process step.

In case the acidic complex compounds contain several free acidic groups, then it is often expedient to produce neutral mixed salts containing inorganic as well as organic cations as the counterions.

This can be done, for example, by reacting the complex-forming acid in an aqueous suspension or solution with the oxide or salt of the element yielding the central ion and with half the amount of an organic base required for neutralization, isolating the thus-formed complex salt, purifying same if desired, and then combining, for complete neutralization, with the required amount of inorganic base. The sequence of base addition can also be reversed.

The conjugates of antibody and complex are dialyzed prior to in vivo utilization after incubation with a weak complexing agent, such as, for example, sodium citrate, sodium ethylenediaminetetraacetic acid, in order to remove weakly bound metal atoms.

In case of using complex compounds which contain radioisotopes, these can be produced in accordance with the methods disclosed in "Radiotracers for Medical Applications", vol. 1, CRC-Press, Boca Raton, Fla.

The pharmaceutical agents of this invention are produced in a likewise conventional way by suspending or dissolving the complex compounds according to this invention—optionally with admixture of the additives customary in galenic pharmacy—in an aqueous medium and subsequently sterilizing the suspension or solution, if necessary. Suitable additives are, for example, physiologically acceptable buffers (e.g. tromethamine), small additions of complexing agents (e.g. diethylenetriaminepentaacetic acid) or, if required, electrolytes, such as, for example, sodium chloride or, if necessary, antioxidants, such as, for example, ascorbic acid.

If, for enteral administration or other purposes, suspensions or solutions of the media of this invention in water or physiological saline solution are desirable, the media are mixed with one or several of the auxiliary agent(s) customary in galenic pharmacy (for example, methylcellulose, lactose, mannitol) and/or tenside(s)(e.g. lecithins, "Tween", "Myrj") and/or aromatizing material(s) for flavor amelioration (for example ethereal oils).

In principle, it is also possible to produce the pharmaceuticals of this invention even without isolation of the Complex salts. In any event, special care must be taken to effect chelate formation so that the salts and salt solutions of this invention are practically devoid of uncomplexed, toxically active metal ions.

This can be ensured, for example, with the aid of color indicators, such as xylenol orange using control titrations during the manufacturing process. Therefore, the invention also relates to processes for preparing the complex compounds and their salts. The final safety measure available is a purification of the isolated complex salt.

The pharmaceutical agents of this invention preferably contain 1 µmol to 1 mol/l of the complex salt and are normally provided in doses amounting to 0.001–5 mmol/kg. They are intended for enteral and parenteral administration.

The complex compounds according to the invention are utilized (1) for NMR and X-ray diagnostics in the form of their complexes with the ions of the elements of atomic numbers 21–29, 42, 44 and 57–83;

(2) for radiodiagnostics and radiotherapy in the form of their complexes with the radioisotopes of the elements of atomic numbers 27, 29, 31, 32, 38, 39, 43, 49, 62, 64, 70 and 77.

The agents of this invention meet the variegated requirements for being suitable as contrast media for nucelar spin tomography. Thus, they are excellently suited for improving the informative content of the image obtained with the, aid of the nuclear spin tomograph upon oral or parenteral administration, by enhancing signal intensity. Furthermore, they exhibit the high efficacy necessary for burdening the body with minimum quantities of foreign substances, and they show the good compatibility required for maintaining the noninvasive character of the examinations.

The good water solubility of the media according to this invention makes it possible to prepare highly concentrated solutions, thus maintaining the volume load on the circulation within tolerable limits and compensating for dilution by body fluids; in other words, NMR diagnostic media must have a water solubility that is 100 to 1000 times higher than for NMR spectroscopy. Furthermore, the media of this invention exhibit not only high stability in vitro, but also a surprisingly high stability in vivo so that release or exchange of the ions—toxic per se—not bound in a covalent fashion in the complexes takes place only extremely gradually within the time period during which the novel contrast media are again completely eliminated.

In general, the media of this invention are utilized as NMR diagnostic agents in doses amounting to 0.001–5 mmol/kg, preferably 0.005–0.5 mmol/kg. Details of use are discussed, for example, in H. J. Weinmann et al., Am. J. of Roentgenology 142: 619 (1984).

Especially low doses (below 1 mg/kg of body weight) of organ-specific NMR diagnostica are usable, for example, for the detection of tumors and of cardiac infarction.

The complex compounds of this invention can furthermore be utilized with advantage as susceptibility reagents and as shift reagents for in vivo NMR spectroscopy.

The media of this invention are likewise suitable as radiodiagnostic agents based on their advantageous radioactive properties and the good stability of the complex compounds contained therein. Details of their usage and dosage can be derived, for example, from "Radiotracers for Medical Applications", CRC-Press, Boca Raton, Fla.

Another imaging method using radioisotopes is positron emission tomography utilizing positron-emitting isotopes, such as, for example, $^{43}$Sc, $^{44}$Sc, $^{52}$Fe, $^{55}$Co and $^{68}$Ga. (Heiss, W. D., Phelps, M. E., Positron Emission Tomography of Brain, Springer Publishers, Berlin, Heidelberg, New York 1983.)

The compounds of this invention can also be used in radioimmunotherapy. This procedure differs from the corresponding diagnostic method merely in the amount and type of the radioactive isotope employed. The objective resides in destruction of tumor cells by high-energy short-wave radiation with a minimum range. The specificity of the antibody utilized is of decisive importance herein since unspecifically localized antibody conjugates result in destruction of healthy tissue.

The antibody or antibody fragment of the antibody-metal complex according to this invention serves for transporting the complex immune-specific for the respective antigen to the target organ where the metal ion, selected on account of its cell-killing properties, can emit radiation inflicting lethal damage to the cells. Suitable β-emitting ions are, for example, $^{46}$Sc, $^{47}$Sc, $^{48}$Sc, $^{72}$Ga and $^{73}$Ga. Examples of α-emitting ions exhibiting suitable low half-life values are $^{211}$Bi, $^{212}$Bi, $^{213}$Bi and $^{214}$Bi, wherein $^{212}$Bi is preferred. A suitable ion emitting photons and electrons is $^{158}$Gd which can be obtained by neutron capture from $^{157}$Gd.

In the in vivo administration of the therapeutic agents according to this invention, they can be administered together with a suitable excipient, such as, for example serum or physiological saline solution and together with another protein, such as, for example, human serum albumin. The dose herein depends on the type of cellular disorder, the metal ion employed, and the type of imaging method.

The therapeutic media of this invention are administered parenterally, preferably intravenously.

Details of the use of radiotherapeutic agents are discussed, for example, in R. W. Kozak et al., TIBTEC, October 1986, 262.

The media according to the invention are excellently suited as X-ray contrast agents; in this connection, it is to be particularly emphasized that they reveal no traces of anaphylaxis-type reactions, known from the iodine-containing contrast media, in biochemical-pharmacological tests. They are of particular value, on account of favorable absorption characteristics in the regions of higher tube voltages, for digital subtraction techniques.

In general, the media of this invention are used, for application as X-ray contrast media, in analogy to, for example, meglumine diatrizoate, in doses amounting to 0.1–5 mmol/kg, preferably 0.25–1 mmol/kg.

Details of utilization of X-ray contrast media are discussed, for example, in Barke, "Röntgenkontrastmittel" [X-Ray Contrast Media], G. Thieme, Leipzig (1970) and P. Thurn, E. Bücheler—"Einführung in die Röntgendiagnostik" [Introduction to X-Ray Diagnostics], G. Thieme, Stuttgart, New York (1977).

In summation, synthesis of novel complexing agents, metal complexes and metal complex salts has been achieved opening up new possibilities in diagnostic and therapeutic medicine. This development appears to be desirable, above all, in light of the evolution of novel imaging processes in medical diagnostics.

The compounds of general Formula I can also be utilized as haptens for the production of antibodies. Details of the application of haptens to the production of antibodies have been described, for example, in S. Sell, Immunology, Immunopathology and Immunity, 372, Harper and Row Publ., 3rd ed.

The examples set forth below serve for a more detailed explanation of the subject matter of this invention.

EXAMPLE 1

(a) 3,6-Diaza-3,6-bis(tert-butoxycarbonylmethyl)-4-(4-hydroxybenzyl)suberic Acid Bis(tertbutyl)diester 15.31 g (0.064 mole) of 4-hydroxybenzyl-1,2-ethanediamine as the dihydrochloride and 71.14 g (0.71 mol) of potassium bicarbonate are provided in 380 ml of dimethylformamide (dried over sodium hydride) and, at 35° C., 50 g (0.26 mol) of bromoacetio acid tert-butyl ester in 80 ml of dimethylformamide is added dropwise thereto. The mixture is stirred for another 2.5 hours at 35° C., whereafter thin-layer chromatography shows no longer any starting compound. The product is filtered off from precipitated potassium bromide and the filtrate is concentrated. The residue is combined with water and repeatedly extracted with ether. After drying and concentration, the ether extract is purified over a silica gel column from unreacted bromoacetic acid tert-butyl ester, thus obtaining 24.8 g (63% of theory) of a colorless oil.

Analysis

Calcd: C 63.64; H 8.73; N 4.49; O 23.12.

Found: C 63.78; H 8.69; N 4.41.

(b) 3,6-Diaza-3,6-bis(tert-butoxycarbonylmethyl)-4-[4-(3-benzyloxycarbonylaminopropoxy) benzyl] suberic Acid Bis(tert-butyl)diester 1.0 g (1.61 millimoles) of 3,6-diaza-3,6-bis(tert-butoxycarbonylmethyl)-4-(4-hydroxybenzyl)suberic acid bis(tert-butyl)diester (Example 1a) is combined with 53 mg of NaH (80% strength in paraffin) (1.77 mmol) in 10 ml of dry tetrahydrofuran, and 440 mg of N-(3-bromopropyl) carbamic acid benzyl ester in 5 ml of tetrahydrofuran is gradually added dropwise to the reaction mixture. After agitation overnight, the mixture is concentrated and separated from paraffin oil through a silica gel column. After evaporation of the solvent, 920 mg (70.2% of theory) of a colorless oil is obtained.

Analysis

Calcd: C 64.92; H 8.29; N 5.16; O 21.61.

Found: C 64.99; H 8.20; N 5.07.

(c) 3,6-Diaza-3,6-bis(tert-butoxycarbonylmethyl)-4-[4-(3-aminopropoxy)benzyl]suberic Acid Bis(tert-butyl)diester 0.92 g (1.13 mmol) of 3,6-diaza-3,6-bis (butoxycarbonylmethyl)-4-[4-(3-benzyloxycarbonyl-aminopropoxy)benzyl]suberic acid bis(tert-butyl)diester (Example 1b)(1.13 mmol) is dissolved in 20 ml of methanol and hydrogenated with 500 mg of 10% palladium-carbon until there is no longer absorption of $H_2$. The mixture is then filtered off from the catalyst. The remaining colorless oil weighs 680 mg (74% of theory).

Analysis

Calcd: C 63.59; H 9.04; N 6.18; O 21.17.

Found: C 63.43; H 8.99; N 6.15.

(d) 3,6-Diaza-3,6-bis (tert-butoxycarbonylmethyl)-4-[4-(3(maleimido)propoxy)benzyl]suberic Acid Bis (tert-butyl)diester 6.5 g of 3,6-diaza-3,6-bis(tert-butoxycarbonylmethyl)-4-[4-(3-aminopropoxy)benzyl]suberic acid bis(tert-butyl) diester (Example 1c)(9.4 mmol) in 200 ml of dry methylene chloride is combined with a solution of 920 mg (9.4 mmol) of maleic anhydride in 50 ml of methylene chloride and stirred overnight at room temperature. Then 1.27 g (9.4 mmol) of 1-hydroxybenzotriazole and 2.13 g (10.34 mmol) of dicyclohexylcarbodiimide are added. After 2 days, the mixture is filtered off from separated urea and the product is purified by preparative medium pressure chromatography (methylene chloride/ether). Yield: 3.89 g (80% of theory)

Analysis

Calcd: C 63.22; H 8.09; N 5.52; O 23.15.

Found: C 63.19; H 8.15; N 5.41.

(e) 3,6-Diaza-3,6-bis (carboxymethyl)-4-[4-(3-(maleimido) propoxy)benzyl]suberic Acid 2.4 g (9.2 mmol) of 3,6-diaza-3,6-bis(tert-butoxycarbonylmethyl)-4-[4-(3-(maleimido)propoxy)-5 benzyl]suberic acid bis(tert-butyl)diester (Example 1d) is dissolved in 35 ml of trifluoroacetic acid and stirred for 36 hours at room temperature. One-half of the trifluoroacetic acid is removed under vacuum and the remaining solution is poured into 100 ml of dry diethyl ether. The thus-precipitated product is suctioned off and dried, yielding 1.45 g (85%) of a white crystalline powder.

Melting point: >145° (decomposition)

Analysis

Calcd: C 53.82; H 5.45; N 7.84; O 32.86.

Found: C 53.89; H 5.41; N 7.85.

Gadolinium Complex 7.25 g (13.55 mmol) of 3,6-diaza-3,6-bis(carboxymethyl)-4-[4-(3-(maleimido)propoxy)benzyl]suberic acid is dissolved in 120 ml of 0.1N ammonium acetate/water and gradually combined with 14 ml of a 1N gadolinium acetate solution in water. After 15 minutes the mixture is adjusted to a pH of about 7.5–8 with 0.1N ammonia solution, heated for 15 minutes to 60° C., and then removed by centrifuging. The supernatant yields, after freeze-drying, 9.35 g of white crystalline mass (99% of theory).

Analysis

Calcd: C 41.79; H 3.79; N 6.09; O 25.51 Gd 22.79.

Found: C 41.77; H 3.76; N 6.11; Gd 22.55.

Gd (atomic absorption spectroscopy=AAS): 22.72%

Sodium Salt of the Gadolinium Complex

The complex obtained as described above (3.63 g; 5.26 mmol) is dissolved in ten times the amount of water and combined by means of a micro-burette with 5.26 ml of a 1N sodium hydroxide solution. After freeze-drying, 3.74 g of white crystals is obtained.

Analysis

Calcd: C 40.44; H 3.67; N 5.89; O 24.69; Gd 22.06; Na 3.22.

Found: C 40.32; H 3.60; N 5.95; O; Gd 21.81; Na 3.33.

N-Methyl-D-glucamine Salt of the Gadolinium Complex 7.85 g (11.38 mmol) of the gadolinium complex dissolved in 80 ml of water is combined with 2.22 g (11.38 mmol) of N-methyl-D-glucamine under agitation, in incremental portions. After complete dissolution of the base, the mixture is freeze-dried. There remains 10.0 g of a colorless crystalline compound.

Analysis

Calcd: C 42.07; H 4.89; N 6.53; O 28.92; Gd 17.76.
Found: C 42.12; H 4.77; N 6.59; O; Gd 17.77.

Morpholine Salt of the Gadolinium Complex 5.13 g (7.43 mmol) of the gadolinium complex dissolved in 50 ml of water is combined with 6.4 g of a solution containing 10% by weight of morpholine and then freeze-dried, yielding 5.76 g of colorless crystals.

Analysis

Calcd: C 43.34; H 4.41; N 7.22; O 24.74; Gd 20.26.
Found: C 43.40; H 4.32; N 7.41; O; Gd 20.22.

Analogously to the directions for preparing the gadolinium complex, the following are obtained:

Yttrium Complex

Calcd: C 46.31; H 4.21; N 6.75; O 28.28; Y 14.45.
Found: C 46.45; H 4.19; N 6.78; O; Y 14.07.

Ytterbium Complex

Calcd: C 40.86; H 3.71; N 5.96; O 24.95; Yb 24.53.
Found: C 40.83; H 3.81; N 5.87; O; Yb 24.41.

Samarium Complex

Calcd: C 42.21; H 3.84; N 6.16; O 25.77; Sm 22.02.
Found: C 42.17; H 3.82; N 6.05; O; Sm 22.13.

Praseodymium Complex

Calcd: C 42.81; H 3.89; N 6.24; O 26.14; Pr 20.92.
Found: C 42.18; H 3.79; N 6.22; O; Pr 20.97.

Cobalt Complex

Calcd: C 48.74; H 4.43; N 7.11; O 29.76; Co 9.96.
Found: C 48.73; H 4.71; N 7.33; O; Co 10.07.

Indium Complex

Calcd: C 44.53; H 4.05; N 49.31; O 27.19; In 17.74.
Found: C 44.56; H 3.98; N 49.27; In 17.82.

EXAMPLE 2

(a) 3,6-Diaza-3,6-bis(tert-butoxycarbonylmethyl)-4-[4-(3-(methacrylamido)propoxy)benzyl]suberic Acid Bis(tert-butyl)diester 7.33 g (10.6 mmol) of 3,6-diaza-3,6-bis(tert-butoxycarbonylmethyl)-4-[4-(3-aminopropoxy)benzyl]suberic acid bis(tert-butyl)diester (Example 1c) dissolved in 175 ml of dry ethyl acetate is combined with 1.2 ml (11.7 mmol) of triethylamine and, at 0° C., a solution of 1.2 g (11 mmol) of methacryloyl chloride in 20 ml of dry ethyl acetate is added dropwise thereto. The mixture is stirred overnight at room temperature, then filtered off from precipitated triethylammonium chloride, and concentrated. After column chromatography (toluene/ethyl acetate), 6.9 g (9.2 mmol; 87% of theory) of a colorless oil is obtained.

Analysis

Calcd: C 64.23; H 8.75; N 5.61 0.21.39.
Found: C 64.44; H 8.52; N 5.63

(b) 3,6-Diaza-3,6-bis(carboxymethyl)-4-[4-(3-(methacrylamido)propoxy)benzyl]suberic Acid As described in Example 1e, 2.0 g (2.7 mmol) of 3,6-diaza-3,6-bis(tert-butoxycarbonylmethyl)-4-[4-(3-(methacrylamido)propoxy)benzyl]suberic acid bis(tert-butyl)diester (Example 2a) is converted with trifluoroacetic acid into the free complexing agent. After drying, 1.3 g (2.5 mmol; 92%) of a colorless powder is obtained.

Melting point: 133° C. (decomposition)

Analysis

Calcd: C 55.06; H 6.35; N 8.02; O 30.55.
Found: C 55.01; H 6.23; N 8.13.

Gadolinium Complex

In analogy to the directions in Example 1e, the gadolinium complex is obtained in almost quantitative yield.

Analysis

Calcd: C 42.53; H 4.46; N 6.19; O 23.6; Gd 23.20.
Found: C 42.38; H 4.30; N 6.25; Gd 23.02.
Gd (AAS): 23.25%.

Analogously to the directions in 1e, the following salts are obtained:

Sodium Salt of the Gadolinium Complex

Calcd: C 41.13; H 4.31; N 5.99; O 22.83; Gd 22.44; Na 3.28.
Found: C 41.20; H 4.39; N 5.89; O; Gd 21.99; Na 3.27.

Meglumine Salt of the Gadolinium Complex

Calcd: C 43.96; H 5.13; N 7.32; O 23.00; Gd 20.55.
Found: C 43.89; H 5.22; N 7.30; O; Gd 21.01.

Morpholine Salt of the Gadolinium Complex

Calcd: C 42.60; H 5.53; N 6.41; O 27.45; Gd 17.99.
Found: C 42.65; H 5.60; N 6.42; O; Gd 17.79.

EXAMPLE 3

(a) 3,6-Diaza-3,6-bis(tert-butoxycaronylmethyl)-4-(4-benzyloxycarbonylmethoxybenzyl)suberic Acid Bis(tert-butyl)diester 93.06 g of 3,6-diaza-3,6-bis(tert-butoxy-carbonylmethyl)-4-(4-hydroxybenzyl)suberic acid bis(tert-butyl)diester (Example 1a)(0.15 mol) is gradually combined with 4.48 g of NaH (80% in paraffin)(0.15 mol) in 600 ml of dry tetrahydrofuran under agitation, and then, at room temperature, 34.4 g of bromoacetic acid benzyl ester (0.15 mol) in 150 ml of dry tetrahydrofuran is added dropwise thereto. After agitation overnight, the mixture is suctioned off from precipitated sodium bromide, concentrated, taken up in diethyl ether, and the remaining inorganic components are removed by washing with water. After drying with $MgSO_4$, the product is freed of solvent and purified over a silica gel column, thus obtaining 75.2 g (65% of theory) of a colorless oil.

Analysis

Calcd: C 65.43; H 8.10; N 3.63; O 22.82.
Found: C 65.23; H 8.17; N 3.58.

(b) 3,6-Diaza-3,6-bis(carboxymethyl)-4-(4-benzyloxycarbonylmethoxybenzyl)suberic Acid 5.49 g of 3,6-diaza-3,6-bis(tert-butoxycarbonylmethyl)-4-(4benzyloxycarbonylmethoxybenzyl)suberic acid bis(tert-butyl)diester (Example 3a) (8.1 mmol) is heated to 50° C. in 50 ml of trifluoroacetic acid and allowed to stand overnight at room temperature. Then the clear solution is poured into 500 ml of dry ether and the precipitate is suctioned off. After drying, 2.4 g of white crystals is obtained (54.5% of theory), decomposing with gas evolution starting at 150° C.

Analysis

Calcd: C 57.13; H 5.53; N 5.12; O 32.20.
Found: C 57.21; H 5.51; N 4.98.

The gadolinium complex is produced using the procedure described in Example 1e.

Analysis

Calcd: C 44.56; H 3.88; N 3.99; O 25.11; Gd 22.43.
Found: C 44.42; H 3.85; N 4.05; Gd 21.93.
Gd (AAS): 22.38%.

The following salts are likewise obtained pursuant to the process disclosed in 1e:

Sodium Salt of the Gadolinium Complex
Analysis
Calcd: C 43.20; H 3.62; N 3.87; O 24.35; Gd 21.75; Na 3.18.
Found: C 43.14; H 3.66; N 3.85; O; Gd 21.15; Na 3.09.
Meglumine Salt of the Gadolinium Complex
Analysis
Calcd: C 44.28; H 4.84; N 4.69; O 28.60; Gd 17.57.
Found: C 44.30; H 4.81; N 4.75; O; Gd 17.23.
Morpholine Salt of the Gadolinium Complex
Analysis
Calcd: C 45.79; H 4.48; N 5.34; O 24.39; Gd 19.98.
Found: C 45.81; H 4.41; N 5.37; O; Gd 19.59.

EXAMPLE 4

(a) 3,6-Diaza-3,6-bis(tert-butoxycarbonylmethyl)-4-(4-hydrazinocarbonylmethoxybenzyl)suberic Acid Bis(tert-butyl)diester 6.8 g of 3,6-diaza-3,6-bis(tert-butoxycarbonyl-methyl)-4-(4-benzyloxycarbonylmethoxybenzyl)suberic acid bis(tert-butyl)diester (Example 3a)(8.82 mmol) dissolved in 25 ml of absolute ethanol is added dropwise to a solution of 1.1 ml of hydrazine hydrate (22.3 mmol) in 50 ml of ethanol at 5° C.–10° C. and stirred overnight at room temperature. Then the mixture is concentrated to half the amount, poured into 400 ml of H$_2$O and repeatedly extracted with ether. After drying and evaporation of the organic phase, the product is purified via a silica gel column, thus obtaining 5.85 g (95.4% of theory) of a colorless oil.

Analysis
Calcd: C 60.49; H 8.41; N 8.06; O 23.02.
Found: C 60.60; H 8.31; N 8.07.

(b) 3,6-Diaza-3,6-bis(carboxymethyl)-4-(4-hydrazinocarbonylmethoxybenzyl)suberic Acid 7.7 g (10.9 mmol) of 3,6-diaza-3,6-bis(tert-butoxycarbonylmethyl)-4-(4-hydrazinocarbonylmethoxybenzyl)suberic acid bis(tert-butyl)diester (Example 4a) is allowed to stand in 80 ml of trifluoroacetic acid for 2 hours at room temperature. Then the mixture is poured into dry ether and decanted. Thereafter, the mixture is stirred for another half hour with 100 ml of a 10% ether-triethylamine solution, suctioned off, and dried under vacuum: 4.5 g of white crystals, melting point 185° C. (decomposition). Yield: 4.5 g (89% of theory).

Analysis
Calcd: C 48.50; H 5.57; N 11.90; O 34.0.
Found: C 48.27; H 5.56; N 11.93.

The gadolinium complex is prepared according to the procedure described in Example 1e.

Analysis
Calcd: C 36.53; H 3.71; N 8.96; O 25.61; Gd 25.17.
Found: C 36.60; H 3.68; N 8.89; Gd 24.51.
Gd (AAS): 25.26%.

The following salts are obtained analogously to the directions in Example 1e:
Sodium Salt of the Gadolinium Complex
Analysis
Calcd: C 35.29; H 3.42; N 8.66; O 24.74; Gd 24.31; Na 3.55.
Found: C 35.33; H 3.40; N 8.71; O; Gd 24.01; Na 3.59.
Meglumine Salt of the Gadolinium Complex
Analysis
Calcd: C 38.08; H 4.91; N 8.54; O 29.27; Gd 19.17.
Found: C 38.12; H 4.90; N 8.49; O; Gd 19.20.
Morpholine Salt of the Gadolinium Complex
Analysis
Calcd: C 38.86; H 4.39; N 9.85; O 24.76; Gd 22.12.
Found: C 38.82; H 4.48; N 9.89; O; Gd 22.16.

EXAMPLE 5

(a) 3,6-Diaza-3,6-bis(tert-butoxycarbonylmethyl)-4-(4-benzyloxycarbonylpentamethylenoxybenzyl)suberic Acid Bis(tert-butyl)diester According to the directions given for Example 3a, 3.5 g (5.6 mmol) of 3,6-diaza-3,6-bis(tert-butoxycarbonylmethyl)-4-(4-hydroxybenzyl)suberic acid bis(tert-butyl)diester (Example 1a) and 1.6 g (5.6 mmol) of 6-bromocaproic acid benzyl ester yield 3.6 g (78% of theory) of a colorless oil.

Analysis
Calcd: C 66.80; H 8.53; N 3.38; O 21.27.
Found: C 66.72; H 8.49; N 3.40.

(b) 3,6-Diaza-3,6-bis(carboxymethyl)-4-(4-benzyloxycarbonylpentamethylenoxybenzyl)suberic Acid In accordance with the directions given for Example 3b, 12.3 g (14.8 mmol) of 3,6-diaza-3,6-bis(tert-butoxycarbonylmethyl)-4-(4-benzyloxycarbonylpentamethylenoxybenzyl)suberic acid bis(tert-butyl)diester (Example 5a) yields 8.25 g (92% of theory) of a white crystallized product.

Melting point: 188° C. (decomposition)
Analysis
Calcd: C 59.79; H 6.35; N 4.64; O 29.20.
Found: C 55.92; H 6.41; N 4.74.
Gadolinium Complex In accordance with the procedure disclosed in Example 1e, the gadolinium complex is obtained in an almost quantitative yield.

Analysis
Calcd: C 47.60; H 4.66; N 3.70; O 23.25; Gd 20.77.
Found: C 47.38; H 4.67; N 3.52; Gd 20.65.

The following salts are obtained analogously to the directions given in Example 1e:
Sodium Salt of the Gadolinium Complex
Analysis
Calcd: C 46.26; H 4.40; N 3.59; O 22.29; Gd 20.19; Na 2.95.
Found: C 46.25; H 4.36; N 3.60; O; Gd 20.09; Na 2.99.
Meglumine Salt of the Gadolinium Complex
Analysis
Calcd: C 47.47; H 5.59; N 4.48; O 25.63; Gd 16.79.
Found: C 47.39; H 5.57; N 4.49; O; Gd 16.63.
Morpholine Salt of the Gadolinium Complex
Analysis
Calcd: C 48.44; H 5.14; N 4.98; O 22.77; Gd 18.65.
Found: C 48.38; H 5.17; N 4.93; O; Gd 18.37.

EXAMPLE 6

(a) 3,6-Diaza-3,6-bis(tert-butoxycarbonylmethyl)-4-(4-hydrazinocarbonylpentamethylenoxybenzyl)suberic Acid Bis(tert-butyl)diester In accordance with the directions indicated for Example 4a, 6.35 g (7.68 mmol) of 3,6-diaza-3,6-bis(tert-butoxycarbonylmethyl)-4-(4- benzyloxycarbonylpentamethylenoxybenzyl)suberic acid bis(tert-butyl)diester (Example 5a) yields 5.07 g (88% of theory) of a colorless oil.

Analyse

Calcd: C 62.37; H 8.85; N 7.46; O 21.30.

Found: C 62.28; H 8.84; N 7.51.

(b) 3,6-Diaza-3,6-bis(carboxymethyl)-4-(4-hydrazinocarbonylpentamethylenoxybenzyl)suberic Acid According to the directions given for Example 4b, 2.66 g 13.54 mmol) of 3,6-diaza-3,6-bis(tert-butoxycarbonylmethyl)-4-(4-hydrazinocarbonylpentamethylenoxybenzyl)suberic acid bis (tert-butyl)diester (Example 6a) yields 1.69 g (91% of theory) of a white crystallized product.

Melting point: 210° C. (decomposition).

Analysis

Calcd: C 52.46; H 6.50; N 10.64; O 30.38.

Found: C 52.51; H 6.39; N 10.70.

Gadolinium Complex

In accordance with the procedure described in Example 1e, the gadolinium complex is obtained in an almost quantitative yield.

Analysis

Calcd: C 40.57; H 4.59; N 8.22; O 23.50; Gd 23.09.

Found: C 40.60; H 4.52; N 8.21; Gd 23.0.

The following salts are obtained analogously to the directions in 1e:

Sodium Salt of the Gadolinium Complex

Analysis

Calcd: C 39.31; H 4.30; N 7.97; O 22.76; Gd 22.37; Na 3.27.

Found: C 39.26; H 4.31; N 7.90; O; Gd 21.97; Na 3.27.

Meglumine Salt of the Gadolinium Complex

Analysis

Calcd: C 41.13; H 5.52; N 7.99; O 27.39; Gd 17.95.

Found: C 41.20; H 5.55; N 7.87; O; Gd 17.81.

Morpholine Salt of the Gadolinium Complex

Analysis

Calcd: C 42.28; H 5.12; N 9.13; O 22.94; Gd 20.50.

Found: C 42.31; H 5.07; N 9.14; O; Gd 20.11.

EXAMPLE 7

(a) 3,6-Diaza-3,6-bis(tert-butoxycarbonylmethyl)-4-[4-(methacryloyl)hydrazinocarbonylpentamethylenoxybenzyl]suberic Acid Bis(tert-butyl)diester 4.17 g (5.56 mmol) of 3,6-diaza-3,6-bis(tert-butoxycarbonylmethyl)-4-(4-hydrazinocarbonylpentamethylenoxybenzyl)suberic acid bis (tert-butyl)diester (Example 6a) is dissolved in 50 ml of dry dichloromethane and combined with 0.6 ml of triethylamine. Then, at 0° C., a solution of 0.6 g of methacryloyl chloride in 10 ml of dichloromethane is added, the mixture is stirred overnight at room temperature, and precipitated triethylammonium chloride is removed by filtration. After filtering over silica gel with ethyl acetate, 3.14 g (69% of theory) of a colorless oil is obtained after evaporation of the solvent.

Analysis

Calcd: C 63.05; H 8.61; N 6.84; O 21.48.

Found: C 62.98; H 8.70; N 6.82.

(b) 3,6-Diaza-3,6-bis(carboxymethyl)-4-[4-(methacryloyl)hydrazinocarbonylpentamethylenoxybenzyl]suberic Acid In accordance with the directions set forth for Example 3b, 3.0 g (3.66 mmol) of 3,6-diaza-3,6-bis(tert-butoxycarbonylmethyl)-4-[4-(methacryloyl)hydrazinocarbonylpentamethylenoxybenzyl]suberic acid bis (tert-butyl)diester (Example 7a) yields 1.92 g (88% of theory) of a white crystallized product.

Melting point: 135° C. (decomposition).

Analysis

Calcd: C 54.53; H 6.44; N 9.42; O 29.59.

Found: C 54.60; H 6.13; N 9.51.

Gadolinium Conmplex

According to the process described in Example 1e, the gadolinium complex is obtained in an almost quantitative yield.

Analysis

Calcd: C 43.30; H 4.71; N 7.48; O 23.50; Gd 20.99.

Found: C 43.24; H 4.69; N 7.43; Gd 21.20.

Analogously to direction 1e, the following salts are obtained:

Sodium Salt of the Gadolinium complex

Analysis

Calcd: C 42.01; H 4.57; N 7.25; O 22.80; Gd 20.37; Na 2.97.

Found: C 41.96; H 4.55; N 7.30; O; Gd 20.03; Na 3.01.

Meglumine Salt of the Gadolinium Complex

Analysis

Calcd: C 43.21; H 5.65; N 7.41; O 27.08; Gd 16.63.

Found: C 43.20; H 5.70; N 7.38; O; Gd 16.33.

Morpholine Salt of the Gadolinium Complex

Analysis

Calcd: C 44.54; H 5.30; N 8.37; O 22.96; Gd 18.81.

Found: C 44.45; H 5.38; N 8.34; O; Gd 18.80.

EXAMPLE 8

(a) 3,6-Diaza-3,6-bis(tert-butoxycarbonylmethyl)-4-(4-carboxymethoxybenzyl)suberic Acid Bis(tert-butyl)diester 9.5 g of 3,6-diaza-3,6-bis(tert-butoxycarbonylmethyl)-4-(4-benzyloxycarbonylmethoxybenzyl)suberic acid bis(tert-butyl)diester (Example 3a)(0.012 mol) is dissolved in 100 ml of anhydrous tetrahydrofuran and hydrogenated in the presence of 2 g of 10% Pd/C until there is no longer any hydrogen absorption. After the mixture has been suctioned off, the solvent is removed using a rotary evaporator and the compound is further dried at 0.01 torr. The resultant viscous oil weighs 8.33 g (99% of theory).

Analysis

Calcd: C 61.74; H 8.29; N 4.11; O 25.84.

Found: C 61.82; H 8.17; N 4.12.

(b) 3,6-Diaza-3,6-bis(tert-butoxycarbonylmethyl)-4-[4-[(2,3,4,5,6-pentahydroxyhexyl)methylamino]carbonylmethoxybenzyl]suberic Acid Bis(tert-butyl) diester 1.36 g of 3,6-diaza-3,6-bis(tert-butoxycarbonylmethyl)-4-(4-carboxymethoxybenzyl)suberic acid bis(tert-butyl) diester is dissolved in 50 ml of tetrahydrofuran and combined with 0.3 g (3 mmol) of triethylamine. At −5° C., 0.29 g (2.02 mmol) of chloroformic acid isobutyl ester in 20 ml of tetrahydrofuran is gently added and finally the mixture is combined with 5 ml of an aqueous solution of 430 mg (2.2 mmol) of N-methyl-D-glucamine. After 30 minutes of agitation at 0° C., the cooling bath is removed and the mixture is allowed to warm up to room temperature. After evaporation of the solvent, the residue is purified by chromatography on silica gel, thus obtaining 1.43 g of a white crystalline compound (83% of theory) decomposing under brown discoloration starting with 52° C.

Analysis

Calcd: C 58.79; H 8.34; N 4.89; O 27.96.

Found: C 58.62; H 8.32; N 4.79.

(c) 3,6-Diaza-3,6-bis(carboxymethyl)-4-[4-[(2,3,4,5,
6-pentahydroxyhexyl)methylamino]
carbonylmethoxybenzyl]suberic Acid As described in Example 1e, 0.78 g (0.91 mmol) of 3,6-diaza-3,6-bis(tert-butoxycarbonylmethyl)-4-[4-[(2,3,4,5,6-pentahydroxyhexyl)methylamino] carbonylmethoxybenzyl]suberic acid bis(tert-butyl)diester yields 432 mg (75% of theory) of the title compound, melting point 132° (decomposition).

Analysis

Calcd: C 49.28; H 6.20; N 6.63; O 37.87.

Found: C 49.19; H 6.21; N 6.46.

Gadolinium Complex

The gadolinium complex is obtained in an almost quantitative yield analogously to the directions in 1e:

Analysis

Calcd: C 39.36; H 4.6; N 5.33; O 30.46; Gd 19.95.

Found: C 39.72; H 4.66; N 5.32; Gd 19.75.

Gd (AAS): 20.01% by weight.

Analogously to the directions of 1e, the following compounds are likewise obtained:

Sodium Salt of the Gadolinium Complex

Analysis

Calcd: C 38.56; H 4.35; N 5.18; O 29.63; Gd 19.41; Na 2.83.

Found: C 38.50; H 4.34; N 5.09; Gd 19.50; Na 2.81.

Meglumine Salt of the Gadolinium Complex

Analysis

Calcd: C 40.31; H 5.43; N 5.69; O 32.55; Gd 15.99.

Found: C 40.29; H 5.40; N 5.67; Gd 15.80.

Morpholine Salt of the Gadolinium Complex

Analysis

Calcd: C 41.23; H 5.07; N 6.41; O 29.29; Gd 17.99.

Found: C 41.20; H 4.98; N 6.37; Gd 17.69.

EXAMPLE 9

(a) O-Benzyl-N-trifluoroacetyltyrosine 112.5 g (0.41 mmol) of O-benzyltyrosine is suspended in 1 liter of dry methanol and combined at room temperature with 58.9 ml (0.42 mol) of triethylamine. After adding 67 ml (0.53 mol) of trifluoroacetic acid ethyl ester, the mixture is stirred at room temperature for 130 hours under exclusion of moisture. The mixture is separated from unreacted starting material and volatile components are removed by shaking with ethyl acetate/aqueous hydrochloric acid. The ethyl acetate phase is decolorized with activated carbon. Evaporation of the solvents yields 120.7 g (80% of theory) of colorless crystals.

Melting point: 149°–150° C.

Analysis

Calcd: C 58.85; H 4.39; N 3.81; O 17.42; F 15.51.

Found: C 58.78; H 4.29; N 3.79; F 15.57.

(b) O-Benzyl-N-trifluoroacetyltyrosine-(2-
carbobenzoxyaminoethylen)amide 18.5 g (50.4 mmol) of O-benzyl-N-trifluoroacetyltyrosine (Example 9a) is dissolved in 200 ml of dry tetrahydrofuran, combined with 7 ml of Et3N, and then 4.8 ml (50.8 mmol) of chloroformic acid ethyl ester is added dropwise while maintaining the temperature at below −10° C. After this adding step is completed, the mixture is agitated for 30 minutes at this temperature, again combined with the same amount of precooled triethylamine, and an ice-cold solution of 11.6 g (50.4 mmol) of N-(2-aminoethyl)carbamic acid benzyl ester hydrochloride in 100 ml of dimethylformamide is added dropwise. The mixture is stirred for another 30 minutes at −10° C., then allowed to warm up to room temperature under agitation, and thereafter heated for 10 minutes to 30° C. Then the solvent is removed by rotary evaporator and the mixture poured on 750 ml of ice water. The crystallized product is suctioned off, washed with ice water, and dried. The yield is 26.9 g (94% of theory).

Melting point: 189°–190° C.

Analysis

Calcd: C 61.87; H 5.19; N 7.73; O 14.71; F 10.48.

Found: C 61.90; H 5.08; N 7.77; F 10.43.

(c) O-Benzyltyrosine-(2-
carbobenzoxyaminoethylen)amide 25.9 g (47.8 mmol) of O-benzyl-N-trifluoroacetyltyrosine-(2-carbobenzoxyaminoethylen) amide (Example 9b) is suspended in 300 ml of EtOH and combined in portions with 7.2 g (191 mmol) of sodium borohydride. After agitation overnight at room temperature, the mixture is combined with 50 ml of acetone, freed of solvent, mixed with 500 ml of $H_2O$, and repeatedly extracted with ethyl acetate. The organic phase yields, after drying and concentration, 18.8 g (88% of theory) of white crystals, melting point 145° C.

Analysis

Calcd: C 69.77; H 6.53; N 9.38; O 14.29.

Found: C 69.79; H 6.53; N 9.35.

(d) Tyrosine-(2-aminoethylen) amide 42.3 g (94.6 mmol) of O-benzyltyrosine-(2-carbobenzoxyaminoethylen)amide (Example 9c) is dissolved in 1.1 liter of methanol, 2 g of 10% palladium-carbon is added, and the mixture is hydrogenated under agitation until hydrogen absorption has ceased. The catalyst is filtered off and the solvent evaporated. The mixture is dissolved in methanol under heating and precipitated with ether: 17 g (86% of theory) of colorless crystals.

Melting point: 138°–141° C.

Analysis

Calcd: C 59.17; H 7.67; N 18.81; O 14.33.

Found: C 59.23; H 7.51; N 18.90.

(e) 3-Aza-1-(4-hydroxybenzyl)pentane-1,5-
diamine•Trihydrochloride 6.55 g (29.3 mmol) of tyrosine-(2-amino-ethylen)amide (Example 9d) is suspended in 130 ml of dry tetrahydrofuran, and a gradual stream of $B_2H_6$(from 5.8 g of $NaBH_4$ in 75 ml of diethylene glycol dimethyl ether and. 54 ml of boron trifluoride etherate complex) is passed with dry nitrogen under continuous agitation through the solution. The mixture is stirred overnight at 60° C., then at 20° C. 30 ml of methanol is added dropwise and, under ice cooling, hydrogen chloride is introduced. Then the mixture is briefly boiled and suctioned off. The trihydrochloride is obtained in the form of colorless crystals (8.04 g; 86% of theory).

Melting point: 250° C. (decomposition)

Analysis

Calcd: C 41.45; H 6.95; N 13.18; O 5.02; Cl 33.37.
Found: C 41.37; H 6.89; N 13.14; Cl 33.51.

(f) 3,6,9-Triaza-4-(4-hydroxybenzyl)-3,6,9-tris(tert-butoxycarbonylmethyl)undecanedioic Acid Bis(tert-butyl)diester 2.07 g (6.5 mmol) of 3-aza-1-(4-hydroxybenzyl)pentane-1,5-diamine•trihydrochloride (Example 9e) is produced with 5.2 g of sodium bicarbonate and 6.34 g (82.2 mmol) of bromoacetic acid tert-butyl ester according to the directions for 3,6-diaza-bis(tert-butoxycarbonylmethyl)-4-(4-hydroxybenzyl)suberic acid bis(tert-butyl)diester (Example 1a), thus obtaining 3.54 g (68.8% of a colorless oil.

Analysis

Calcd: C 63.13; H 8.91; N 5.38; O 22.56.
Found: C 63.21; H 8.90; N 5.42.

(g) 3,6,9-Triaza-3,6,9-tris(tert-butoxycarbonylmethyl)-4-[4-(3-benzyloxycarbonylaminopropoxy)benzyl]undecanedioic Acid Bis(tert-butyl)diester From 4.6 g (5.90 mmol) of 3,6,9-triaza-3,6,9-tris(tert-butoxycarbonylmethyl)-4-(4-hydroxybenzyl)undecanedioic acid bis(tert-butyl)diester (Example 9f), following the directions indicated for Example 1b, 4.2 g of a colorless oil (yield 74% of theory) is obtained.

Analysis

Calcd: C 64.30; H 8.51; N 5.76; O 21.41.
Found: C 64.20; H 8.65; N 5.82.

(h) 3,6,9-Triaza-3,6,9-tris(tert-butoxycarbonylmethyl)-4-[4-(3-aminopropoxy)benzyl]undecanedioic Acid Bis(tert-butyl)diester In accordance with the method described in Example 1c, 3.9 g (4.8 mmol) of 3,6,9-triaza-3,6,9-tris(tert-butoxycarbonylmethyl)-4-[4-(3-benzyloxycarbonylaminopropoxy)benzyl]undecanedioic acid bis(tert-butyl)diester (Example 9g) is hydrogenated. A colorless, viscous oil is obtained. Yield: 3.17 g (97.3% of theory).

Analysis

Calcd: C 63.13; H 9.15; N 6.69; O 21.02.
Found: C 62.97; H 9.01; N 6.62.

(i) 3,6,9-Triaza-3,6,9-tris(tert-butoxycarbonylmethyl)-4-[4-(3-(maleimido)propoxy)benzyl]undecanedioic Acid Bis(tert-butyl)diester In accordance with the procedure described in Example 1d, the maleimide is obtained in a 91% yield (colorless, viscous oil), starting with 3,6,9-triaza-3,6,9-tris(tert-butoxycarbonylmethyl)-4-[4-(3-aminopropoxy)benzyl]undecanedioic acid bis(tert-butyl)diester (Example 9h).

Analysis

Calcd: C 62.86; H 8.35; N 6.10; O 22.62.
Found: C 62.71; H 8.33; N 6.10.

(j) 3,6,9-Triaza-3,6,9-tris(carboxymethyl)-4-[4-(3-(maleimido)propoxy)benzyl]undecanedioic Acid As disclosed in Example 1e, the free penta acid is obtained in an 89% yield, starting with 3,6,9-triaza-3,6,9-tris(tert-butoxycarbonylmethyl)i4-[4-(3-(maleimido)propoxy)benzyl]undecanedioic acid bis(tert-butyl)diester (Example 9i), as a white powder.

Melting point: >161° C. (decomposition).

Analysis

Calcd: C 52.82; H 5.69; N 8.80; O 32.67.
Found: C 52.72; H 5.63; N 8.86.

Gadolinium Complex

Analysis of the description in Example 1e, the gadolinium complex is obtained in an almost quantitative yield.

Analysis

Calcd: C 42.52; H 4.20; N 7.08; O 26.30; Gd 19.88.
Found: C 42.58; H 4.29; N 7.83; O; Gd 19.89.
Gd (AAS): 19.73%.

As described in 1e, the following salts are obtained:

Sodium Salt of the Gadolinium Complex

Analysis

Calcd: C 40.28; H 3.74; N 6.71; O 24.91; Gd 18.83; Na 5.50.
Found: C 40.23; H 3.77; N 6.90; O; Gd 18.58; Na 5.47.

Meglumine Salt of the Gadolinium Complex

Analysis

Calcd: C 42.70; H 5.85; N 7.28; O 30.52; Gd 13.63.
Found: C 42.58; H 5.69; N 7.35; Gd 13.51.

Morpholine Salt of the Gadolinium Complex

Analysis

Calcd: C 44.89; H 5.12; N 8.72; O 24.91; Gd 16.32.
Found: C 44.93; H 5.15; N 8.77; Gd 16.15.

In analogy to the direction for preparing the gadolinium complex, the following are obtained:

Indium Complex
  Calcd: C 44.93; H 4.44; N 7.49; O 27.79; In 15.34.
  Found: C 44.94; H 4.61; N 7.44; In 15.32.

Yttrium Complex
  Calcd: C 46.48; H 4.59; N 7.75; O 28.75; Y 12.43.
  Found: C 46.50; H 4.62; N 7.61; Y 12.45.

Ytterbium Complex
  Calcd: C 41.68; H 4.12; N 6.95; O 25.79; Yb 21.45.
  Found: C 41.55; H 4.17; N 6.81; Yb 21.32.

Samarium Complex
  Calcd: C 42.89; H 4.24; N 7.15; O 26.53; Sm 19.18.
  Found: C 42.81; H 4.23; N 7.20; Sm 19.31.

Praseodymium Complex
  Calcd: C 43.42; H 4.29; N 7.24; O 26.86; Pr 18.19.
  Found: C 43.32; H 4.43; N 7.31; Pr 18.20.

Cobalt Complex
  Calcd: C 48.56; H 4.80; N 8.09; O 30.04; Co 8.51.
  Found: C 48.58; H 4.73; N 8.18; Co 8.36.

EXAMPLE 10

(a) 3,6,9-Triaza-4-(4-benzyloxycarbonylmethoxybenzyl)-3,6,9-tris(tert-butoxycarbonylmethyl)undecanedioic Acid Bis(tert-butyl)diester In accordance with the directions given in Example 3a, 1.98 g (2.54 mmol) of 3,6,9-triaza-4-(4-hydroxybenzyl)-3,6,9-tris(tert-butoxycarbonylmethyl)undecanedioic acid bis(tert-butyl)diester (Example 9f) and 0.54 g of bromoacetic acid benzyl ester (2.54 mmol) yield 1.35 g (1.45 mmol) of a colorless syrup (62% of theory).

Analysis

Calcd: C 64.70; H 8.36; N 4.52; O 22.4
Found: C 64.91; H 8.31; N 4.55

(b) 3,6,9-Triaza-3,6,9-tris(carboxymethyl)-4-(4-benzyloxycarbonylmethoxybenzyl)undecanedioic Acid According to the directions given in Example 3b, 5.3 g (5.71 mmol) of 3,6,9-triaza-4-(4- benzyloxycarbonylmethoxybenzyl)-3,6,9-tris(tert-butoxycarbonylmethyl)undecanedioic acid bis(tert-butyl) diester (Example 10a) yields 3g (82% of theory) of a white solid.

Melting point: 145° C. (decomposition).

Analysis

Calcd: C 55.63; H 5.75; N 6.48; O 32.11.

Found: C 55.69; H 5.70; N 6.43.

The gadolinium complex was prepared in accordance with the procedure disclosed in Example 1e.

Analysis

Calcd: C 44.93; H 4.27; N 5.24; O 25.93; Gd 19.61.

Found: C 44.87; H 4.14; N 5.30; Gd 19.41.

Gd (AAS): 19.62%.

The following salts are obtained by following the directions given in 1e:

Sodium Salt of the Gadolinium Complex

Analysis

Calcd: C 42.60; H 3.81; N 4.96; O 24.59; Gd 18.59; Na 5.43.

Found: C 42.54; H 3.87; N 4.99; Gd 18.38; Na 5.47.

Meglumine Salt of the Gadolinium Complex

Analysis

Calcd: C 44.32; H 5.74; N 5.87; O 30.86; Gd 13.18.

Found: C 44.50; H 5.65; N 5.88; Gd 13.07.

Morpholine Salt of the Gadolinium Complex

Analysis

Calcd: C 46.85; H 5.17; N 7.18; O 24.63; Gd 16.14.

Found: C 46.57; H 5.15; N 7.25; Gd 15.97.

EXAMPLE 11

(a) 3,6,9-Triaza-4-(4-hydrazinocarbonylmethoxybenzyl)-3,6,9-tris(tert-butoxycarbonylmethyl)undecanedioic Acid Bis(tert-butyl)diester In accordance with the directions given in Example 4a, 12.6 g (13.57 mmol) of 3,6,9-triaza-4-(4-benzyloxycarbonylmethoxybenzyl)-3,6,9-tris(tert-butoxycarbonylmethyl)undecanedioic acid bis(tert-butyl) diester (Example 10a) yields 9.6 g (83% of theory) of a colorless oil which is highly viscous at room temperature.

Analysis

Calcd: C 60.61; H 8.63; N 8.21; O 22.53.

Found: C 60.47; H 8.70; N 8.12.

(b) 3,6,9-Triaza-3,6,9-tris(carboxymethyl)-4-(4-hydrazinocarbonylmethoxybenzyl)undecanedioic Acid 6.8 g (7.9 mmol) of 3,6,9-triaza-4-(4-hydrazinocarbonylmethoxybenzyl)-3,6,9-tris(tert-butoxycarbonylmethyl)undecanedioic acid bis(tert-butyl) diester (Example a) is reacted with trifluoroacetic acid according to the directions in Example 4b. After the reaction mixture has been worked up, 3.1 g of white crystals is obtained (67% of theory).

Melting point: 180° C. (decomposition).

Analysis

Calcd: C 48.33; H 5.81; N 12.25; O 33.59.

Found: C 48.46; H 5.79; N 12.30.

The gadolinium complex was prepared according to the procedure described in Example 8

Analysis

Calcd: C 33.06; H 4.16; N 9.64; O 26.45; Gd 21.66.

Found: C 32.98; H 4.08; N 9.55; Gd 21.03.

Gd (AAS): 21.57%.

The following salts are obtained in analogy to the directions given in 1e:

Sodium Salt of the Gadolinium Complex

Analysis

Calcd: C 35.88; H 3.66; N 9.09; O 24.94; Gd 20.42; Na 5.97.

Found: C 35.78; H 3.57; N 9.00; Gd 20.23; Na 5.96.

Meglumine Salt of the Gadolinium Complex

Analysis

Calcd: C 39.85; H 5.69; N 8.79; O 31.56; Gd 14.10.

Found: C 39.81; H 5.70; N 8.73; Gd 14.00.

Morpholine Salt of the Gadolinium Complex

Analysis

Calcd: C 41.46; H 5.16; N 10.91; O 24.94; Gd 17.51.

Found: C 41.41; H 5.17; N 10.99; Gd 17.48.

EXAMPLE 12

(a) 3,6,9-Triaza-3,6,9-tris(tert-butoxycarbonylmethyl)-4-(4-benzyloxycarbonylpentamethylenoxybenzyl) undecanedioic Acid Bis(tert-butyl)diester In accordance with the directions given for Example 3a, 7.3 g (9.36 mmol) of 3,6,9-triaza-3,6,9-tris(tert-butoxycarbonylmethyl)-4-(4-hydroxybenzyl)undecanedioic acid bis(tert-butyl)diester (Example 9f) and 2.67 g (9.36 mmol) of 6-bromocaproic acid benzyl ester yield 7.19 g (78% of theory) of a colorless oil.

Analysis

Calcd: C 65.89; H 8.70; N 4.26; O 21.13.

Found: C 65.76; H 8.62; N 4.30.

(b) 3,6,9-Triaza-3,6,9-tris(carboxymethyl)-4-(4-benzyloxycarbonylpentamethylenoxybenzyl) undecanedioic Acid According to the directions given for Example 3b, 6.93 g (7.04 mmol) of 3,6,9-triaza-3,6,9-tris(tert-butoxycarbonylmethyl)-4-(4-benzyloxycarbonylpentamethylenoxybenzyl)undecanedioic acid bis(tert-butyl)diester (Example a) yields 4.30 g (87% of theory) of a white crystallized product.

Melting point: 173° C. (decomposition).

Analysis

Calcd: C 58.02; H 6.44; N 5.97; O 29.55.

Found: C 58.02; H 6.34; N 5.96.

Gadolinium Complex

In accordance with the procedure disclosed in Example 1e, the gadolinium complex is obtained in an almost quantitative yield.

Analysis

Calcd: C 47.59; H 4.93; N 4.89; O 24.24; Gd 18.32.

Found: C 47.50; H 4.83; N 4.98; Gd 18.22.

Analogously to the directions given in 1e, the following salts are obtained:

Sodium Salt of the Gadolinium Complex

Analysis

Calcd: C 45.27; H 4.47; N 4.65; O 23.06; Gd 17.43; Na 5.09.

Found: C 45.33; H 4.45; N 4.61; Gd 17.51; Na 5.11.

Meglumine Salt of the Gadolinium Complex

Analysis

Calcd: C 46.18; H 6.13; N 5.60; O 29.47; Gd 12.59.

Found: C 46.17; H 6.14; N 5.51; Gd 12.61.
Morpholine Salt of the Gadolinium Complex
Analysis
Calcd: C 48.96; H 5.67; N 6.79; O 23.29; Gd 15.26.
Found: C 48.99; H 5.61; N 6.78; Gd 15.17.

EXAMPLE 13

(a) 3,6,9-Triaza-3,6,9-tris(tert-butoxycarbonylmethyl)-4-(4-hydrazinocarbonylpentamethylenoxybenzyl) undecanedioic Acid Bis(tert-butyl)diester According to the directions given in Example 4a, 16.35 g (16.61 mmol) of 3,6,9-triaza-3,6,9-tris(tert-butoxycarbonylmethyl)-4-(4-benzyloxycarbonylpentamethylenoxybenzyl)undecanedioic acid bis(tert-butyl)diester (Example 12a) yields 14.03 g (93% of theory) of a colorless oil.

Analysis
Calcd: C 62.15; H 8.99; N 7.71; O 21.14.
Found: C 62.01; H 8.72; N 7.78.

(b) 3,6,9-Triaza-3,6,9-tris(carboxymethyl)-4-(4-hydrazinocarbonylpentamethylenoxybenzyl) undecanedioic Acid According to the directions set forth for Example 4b, 6.25 g (6.88 mmol) of 3,6,9-triaza-3,6,9-tris(tert-butoxycarbonylmethyl)-4-(4-hydrazinocarbonylpentamethylenoxybenzyl)undecanedioic acid bis(tert-butyl)diester (Example a) yields 3.86 g (87% of theory) of a white crystallized product.

Melting point: 225° C. (decomposition).
Analysis
Calcd: C 51.66; H 6.58; N 11.15; O 30.58.
Found: C 51.52; H 6.57; N 11.20.
Gadolinium Complex According to the procedure described in Example 1e, the gadolinium complex is obtained in an almost quantitative yield.

Analysis
Calcd: C 41.47; H 4.89; N 8.95; O 24.55; Gd 20.11.
Found: C 41.41; H 4.90; N 9.01; Gd 20.12.

The following salts are obtained analogously to the directions given in 1e:
Sodium Salt of the Gadolinium Complex
Analysis
Calcd: C 39.26; H 4.39; N 8.48; O 23.24; Gd 19.04; Na 5.56.
Found: C 39.18; H 4.33; N 8.40; Gd 19.00; Na 5.53.
Meglumine Salt of the Gadolinium Complex
Analysis
Calcd: C 42.00; H 6.19; N 8.36; O 30.02; Gd 13.41.
Found: C 42.10; H 6.15; N 8.33; Gd 13.20.
Morpholine Salt of the Gadolinium Complex
Analysis
Calcd: C 44.06; H 5.70; N 10.27; O 23.47; Gd 16.48.
Found: C 43.95; H 5.71; N 10.23; Gd 16.42.

EXAMPLE 14

(a) 3,6,9-Triaza-3,6,9-tris(tert-butoxycarbonylmethyl)-4-[4-(methacryloyl) hydrazinocarbonylpentamethylenoxybenzyl] undecanedioic Acid Bis(tert-butyl)diester In accordance with the directions given for Example 7a, 7.78 g (8.56 mmol) of 3,6,9-triaza-3,6,9-tris(tert-butoxycarbonylmethyl)-4-(4-hydrazinocarbonylpentamethylenoxybenzyl)undecanedioic acid bis(tert-butyl)diester (Example 13a) yields 6.02 g (72% of theory) of a colorless oil.

Analysis
Calcd: C 62.74; H 8.77; N 7.17; O 21.3.
Found: C 62.51; H 8.80; N 7.20.

(b) 3,6,9-Triaza-3,6,9-tris(carboxymethyl)-4-[4-(methacryloyl) hydrazinocarbonylpentamethylenoxybenzyl] undecanedioic Acid According to the procedure given for Example 3b, 1.98 g (2.02 mmol) of 3,6,9-triaza-3,6,9-tris(tert-butoxycarbonylmethyl)-4-[4-(methacryloyl) hydrazinocarbonylpentamethylenoxybenzyl]undecanedioic acid bis(tert-butyl)diester (Example a) yields 1.38 g (98% of theory) of a white crystallized product.

Melting point: 162° C. (decomposition).
Analysis
Calcd: C 53.51; H 6.51; N 10.06; O 29.89.
Found: C 53.60; H 6.72; N 10.10.
Gadolinium Complex In accordance with the process disclosed in Example 1e, the gadolinium complex is obtained in an almost quantitative yield.

Analysis
Calcd: C 43.80; H 4.98; N 8.23; O 24.47; Gd 18.50.
Found: C 43.71; H 4.81; N 8.09; Gd 18.41.

The following salts are obtained analogously to the directions given in 1e:
Sodium Salt of the Gadolinium Complex
Analysis
Calcd: C 41.60; H 4.61; N 7.82; O 23.24; Gd 17.57; Na 5.13.
Found: C 41.55; H 4.62; N 7.78; Gd 17.50; Na 5.12.
Meglumine Salt of the Gadolinium Complex
Analysis
Calcd: C 43.53; H 6.25; N 7.89; O 29.64; Gd 12.66.
Found: C 43.49; H 6.27; N 7.87; Gd 12.51.
Morpholine Salt of the Gadolinium Complex
Analysis
Calcd: C 45.78; H 5.81; N 9.58; O 23.45; Gd 15.36.
Found: C 45.77; H 5.80; N 9.53; Gd 15.31.

EXAMPLE 15

(a) 3,6,9-Triaza-3,6,9-tris(tert-butoxycarbonylmethyl)-4-[4-(3-(methacrylamido) propoxy)benzyl]undecanedioic Acid Bis(tert-butyl) diester In accordance with the method described in Example 2a, starting with 3,6,9-triaza-3,6,9-tris(tert-butoxycarbonylmethyl)-4-[4-(3-aminopropoxy)benzyl] undecanedioic acid bis(tert-butyl)diester (Example 9h), the title compound is obtained in an 89% yield.

Analysis
Calcd: C 63.69; H 8.90; N 6.18; O 21.21.
Found: C 63.61; H 8.71; N 6.22.

(b) 3,6,9-Triaza-3,6,9-tris(carboxymethyl)-4-[4-(3-(methacrylamido)propoxy)benzyl]undecanedioic Acid According to the directions set forth for Example 2b, starting with 3,6,9-triaza-3,6,9-tris(tert-butoxycarbonylmethyl)-4-[4-(3-(methacrylamido)propoxy)benzyl]undecanedioic acid bis(tert-butyl)diester (Example a), the title compound is obtained in a 90% yield.

Analysis

Calcd: C 53.83; H 6.45; N 8.96; O 30.73.

Found: C 53.75; H 6.25; N 8.90.

Gadolinium Complex

According to the procedure described in Example 1e, the gadolinium complex is obtained in a 98% yield.

Analysis

Calcd: C 43.17; H 4.78; N 7.19; O 24.65; Gd 20.18.

Found: C 43.30; H 4.70; N 7.17; Gd 20.22.

Gd (AAS): 20.25%.

The following salts are obtained in analogy to the method described in 1e:

Sodium Salt of the Gadolinium Complex

Analysis

Calcd: C 40.87; H 4.28; N 6.80; O 23.33; Gd 19.11; Na 5.58.

Found: C 40.85; H 4.23; N 6.74; Gd 19.01; Na 5.55.

Meglumine Salt of the Gadolinium Complex

Analysis

Calcd: C 43.10; H 6.20; N 7.18; O 30.07; Gd 13.43.

Found: C 41.15; H 6.19; N 7.20; Gd 13.28.

Morpholine Salt of the Gadolinium Complex

Analysis

Calcd: C 45.41; H 5.71; N 8.82; O 23.52; Gd 16.51.

Found: C 45.36; H 5.84; N 8.78; Gd 16.39.

EXAMPLE 16

(a) 3,6,9-Triaza-3,6,9-tris(tert-butoxycarbonylmethyl)-4-(4-carboxymethoxybenzyl)undecanedioic Acid Bis(tert-butyl)diester In accordance with the method set forth in Example 8a, 7.83 g (8.43 mmol) of 3,6,9-triaza-4-(4-benzyloxycarbonylmethoxybenzyl)-3,6,9-tris(tert-butoxycarbonylmethyl)undecanedioic acid bis(tert-butyl) diester (Example 10a) yields 4.2 g of a colorless oil (yield 74% of theory).

Analysis

Calcd: C 61.62; H 8.53; N 5.01; O 24.81.

Found: C 61.73; H 8.53; N 5.10.

(b) 3,6,9-Triaza-3,6,9-tris(tert-butoxycarbonylmethyl)-4-[4-(2,3,4,5,6-pentahydroxyhexyl)methylaminocarbonylmethoxybenzyl]undecanedioic Acid Bis(tert-butyl)diester 4.56 g (5.4 mmol) of 3,6,9-triaza-3,6,9-tris-(tert-butoxycarbonylmethyl)-4-(4-carboxymethoxybenzyl)undecanedioic acid bis(tert-butyl)diester is dissolved in 100 ml of tetrahydrofuran and combined with 0.5 g (8 mmol) of triethylamine. At −5° C., 0.73 g (5.5 mmol) of chloroformic acid isobutyl ester in 40 ml of tetrahydrofuran is gently added and finally the mixture is combined with 10 ml of an aqueous solution of 1.08 g (5.5 mmol) of N-methyl-D-glucamine. After 30 minutes of agitation at 0° C., the cooling bath is removed and the mixture allowed to warm up to room temperature. After evaporation of the solvent, the residue is purified by chromatography on silica gel, thus obtaining 4.17 g of white, crystalline compound (76% of theory) decomposing with brown discoloration starting with 50° C.

Analysis

Calcd: C 59.15; H 8.53; N 5.51; O 26.79.

Found: C 59.07; H 8.56; N 5.50.

(c) 3,6,9-Triaza-3,6,9-tris(carboxymethyl)-4-[4-(2,3,4,5,6-pentahydroxyhexyl)methylaminocarbonylmethoxybenzyl]undecanedioic Acid As described in Example 1e, 3.25 g (3.2 mmol) of 3,6,9-triaza-3,6,9-tris(tert-butoxycarbonylmethyl)-4-[4-(2,3,4,5,6-pentahydroxyhexyl)methylaminocarbonylmethoxybenzyl]undecanedioic acid bis(tert-butyl)diester yields 1.86 g (79% of theory) of the title compound having a melting point of 132° C. (decomposition).

Analysis

Calcd: C 49.04; H 6.31; N 7.62; O 37.01.

Found: C 49.19; H 6.21; N 7.46.

Gadolinium Complex

Analogously to the directions in 1e, the gadolinium complex is obtained in an almost quantitative yield:

Analysis

Calcd: C 40.53; H 4.87; N 6.30; O 30.59; Gd 17.68.

Found: C 40.72; H 4.65; N 6.32; Gd 17.75.

Gd (AAS): 17.51% by weight.

The following salts are obtained in analogy to the directions given in 1e:

Sodium Salt of the Gadolinium Complex

Analysis

Calcd: C 38.62; H 4.42; N 6.00; O 29.15; Gd 16.85; Na 4.92.

Found: C 38.68; H 4.48; N 5.93; Gd 16.54; Na 4.98.

Meglumine Salt of the Gadolinium Complex

Analysis

Calcd: C 41.30; H 6.06; N 6.56; O 33.76; Gd 12.29.

Found: C 41.27; H 5.98; N 6.69; Gd 11.90.

Morpholine Salt of the Gadolinium Complex

Analysis

Calcd: C 43.01; H 5.60; N 7.91; O 28.64; Gd 14.81.

Found: C 43.06; H 5.62; N 7.98; Gd 14.88.

EXAMPLE 17

(a) 3-Aza-2-(4-benzyloxybenzyl)-4-oxoglutaric Acid Diamide (Method A)

3.62 g (13.3 mmol) of O-benzyltyrosinamide is refluxed with 2.7 g of ethyl oxamate (23 mmol) for 14 hours in dimethoxyethane. After evaporation of the solvent, the mixture is washed in succession with water, ethanol, and ether. After drying, 2.73 g of white crystals (60% of theory) is obtained.

Melting point: 270° C.

Analysis

Calcd: C 63.33; H 5.61; N 12.30; O 18.74.

Found: C 63.24; H 5.52; N 12.14.

or, according to Method B:

(α) 3-Aza-2-(4-benzyloxybenzyl)-4-oxoglutaric Acid 5-Ethyl Ester 1-Amide 3 g (11.1 mmol) of O-benzyltyrosinamide is dissolved in 30 ml of dimethoxyethane, combined with 1.56 ml of triethylamine, and, at 0° C., 1.53 g (11.1 mmol) of oxalic acid ethyl ester chloride is added dropwise thereto. After 30 minutes at 0° C., the mixture is poured on 100 ml of ice, suctioned off, and dried. The yield is 3.87 g (94% of theory).

Melting point: 142° C.

Analysis

Calcd: C 64.85; H 5.98; N 7.56; O 21.59.
Found: C 64.71; H 6.11; N 7.46.

(β) 3.6 g (9.72 mmol) of 3-aza-2-(4-benzyloxybenzyl)-4-oxoglutaric acid 5-ethyl ester 1-amide (Example aα) is covered by 40 ml of a solution of 1 mole of $NH_3$/l of methanol by pouring the solution thereover. After 1 hour, the thus-precipitated product is filtered off. After drying, 3.13 g (95% of theory) of the title compound is obtained in the form of colorless crystals.
Melting point: 269° C.
Analysis
Calcd: C 63.33; H 5.61; N 12.30; O 18.74.
Found: C 63.25; H 5.63; N 12.17.

(b) 3-Aza-2-(4-hydroxybenzyl)-4-oxoglutaric Acid Diamide

One gram (2.9 mmol) of 3-aza-2-(4-benzyloxybenzyl)-4-oxoglutaric acid diamide (Example a) is suspended in 20 ml of methanol with 100 mg of 10% palladium-carbon and several drops of concentrated hydrochloric acid and hydrogenated until hydrogen absorption has ceased. After filtering the reaction mixture off from the catalyst, 690 mg of colorless crystals is obtained (93% of theory).
Melting point: 245°–250° C. (decomposition).
Analysis
Calcd: C 52.58; H 5.21; N 16.72; O 25.47.
Found: C 52.83; H 5.19 N 16.84.

(c) 3-Aza-2-(4-hydroxybenzyl)pentane-1,5-diamine•Trihydrochloride

One gram (4.0 mmol) of 3-aza-2-(4-hydroxy-benzyl)-4-oxoglutaric acid diamide (Example b) is reacted according to the directions given for Example 9e. The resultant colorless crystallized product weighs 1.19 g (93.7% of theory).
Melting point: 238° C.
Analysis
Calcd: C 41.61; H 6.98; N 13.23; O 5.03; Cl 33.13.
Found: C 41.60; H 6.95; N 13.17; Cl 33.33.

(d) 3,6,9-Triaza-3,6,9-tris(tert-butoxycarbonylmethyl)-5-(4-hydroxybenzyl) undecanedioic Acid Bis(tert-butyl)diester According to the method described in Example 1a, 5.19 g (16.3 mmol) of 3-aza-2-(4-hydroxybenzyl)pentane-1,5-diamine•trihydrochloride (Example c) is reacted to yield 7.75 g (61% of theory) of the title compound in the form of a highly viscous, clear liquid.
Analysis
Calcd: C 63.13; H 8.91; N 5.38; O 22.56.
Found: C 63.00; H 8.92; N 5.29.

(e) 3,6,9-Triaza-5-(4-benzyloxycarbonylmethoxybenzyl)-3,6,9-tris(tert-butoxycarbonylmethyl)undecanedioic Acid Bis(tert-butyl)diester 5.0 g (6.4 mmol) of 3,6,9-triaza-3,6,9-tris(tert-butoxycarbonylmethyl)-5-(4-hydroxybenzyl)undecanedioic acid bis(tert-butyl)diester (Example d) is reacted according to the directions for Example 3a with bromoacetic acid benzyl ester, yielding 4.6 g (74.8% of theory) of a colorless, viscous oil.

Analysis
Calcd: C 64.70; H 8.36; N 4.52; O 22.40.
Found: C 64.46; H 8.30; N 4.49.

(f) 3,6,9-Triaza-3,6,9-tris(carboxymethyl)-5-(4-benzyloxycarbonylmethoxybenzyl)undecanedioic Acid In accordance with the method disclosed in Example 3b, 3.6 g (5.7 mmol) of 3,6,9-triaza-3,6,9-tris(tert-butoxycarbonylmethyl)-5-(4-benzyloxycarbonylmethoxybenzyl)undecanedioic acid bis(tert-butyl)diester (Example 17e) yields 3.9 g (82% of theory) of a white color material.
Melting point: 145° C. (decomposition).
Analysis
Calcd: C 55.63; H 5.75; N 6.48; O 32.11.
Found: C 55.67; H 5.54; N 6.65.

The gadolinium complex was prepared using the method described in Example 1e.
Analysis
Calcd: C 44.93; H 4.27; N 5.24; O 25.93; Gd 19.61.
Found: C 45.01; H 4.21; N 5.15; Gd 19.70.
Gd (AAS): 19.61%.

The following salts are obtained in analogy to the directions given in 1e:
Sodium Salt of the Gadolinium Complex
Analysis
Calcd: C 42.60; H 3.81; N 4.96; O 24.59; Gd 18.59; Na 5.43.
Found: C 42.61; H 3.82; N 4.90; Gd 18.40; Na 5.45.
Meglumine salt of the Gadolinium Complex
Analysis
Calcd: C 44.32; H 5.74; N 5.87; O 30.86; Gd 13.18.
Found: C 44.31; H 5.59; N 5.74; Gd 13.12.
Morpholine Salt of the Gadolinium Complex
Analysis
Calcd: C 46.85; H 5.17; N 7.18; O 24.63; Gd 16.14.
Found: C 46.72; H 5.21; N 7.18; Gd 16.16.

EXAMPLE 18

(a) 3,6,9-Triaza-3,6,9-tris(tert-butoxycarbonylmethyl)-5-[4-(3-benzyloxycarbonylaminopropoxy)benzyl] undecanedioic Acid Bis(tert-butyl)diester 9.6 g (5.90 mmol) of 3,6,9-triaza-3,6,9-tris(tert-butoxycarbonylmethyl)-5-(4-hydroxybenzyl)undecanedioic acid bis(tert-butyl)diester (Example 17d) yields, by following the directions given for Example 1b, 4.2 g of a colorless oil (yield 74% of theory).
Analysis
Calcd: C 64.30; H 8.51; N 5.76; O 21.41.
Found: C 64.45; H 8.55; N 5.76.

(b) 3,6,9-Triaza-3,6,9-tris(tert-butoxycarbonylmethyl)-5-[4-(3-aminopropoxy) benzyl]undecanedioic Acid Bis(tert-butyl)diester In accordance with the method described in Example 1c, 2.8 g (1.25 mmol) of 3,6,9-triaza-3,6,9-tris(tert-butoxycarbonylmethyl)-5-[4-(3-benzyloxycarbonylaminopropoxy)benzyl]undecanedioic acid bis(tert-butyl)diester (Example a) is hydrogenated, thus obtaining a colorless, viscous oil.

Yield: 2.28 g (95% of theory).
Analysis
Calcd: C 63.13; H 9.15; N 6.69; O 21.02.
Found: C 63.22; H 9.14; N 6.66.

(c) 3,6,9-Triaza-3,6,9-tris(tert-butoxycarbonylmethyl)-5-[4-(3-(maleimido)propoxy)benzyl]undecanedioic Acid Bis(tert-butyl) diester According to the method described in Example 1d, starting with 3,6,9-triaza-3,6,9-tris(tert-butoxycarbonylmethyl)-5-[4-(3-aminopropoxy)benzyl]undecanedioic acid bis(tert-butyl)diester (Example b), the maleimide is obtained in a 90% yield (colorless, viscous oil).
Analysis
Calcd: C 62.86; H 8.35; N 6.10; O 22.62.
Found: C 62.75; H 8.41; N 6.01.

(d) 3,6,9-Triaza-3,6,9-tris(carboxymethyl)-5-[4-(3-(maleimido)propoxy)benzyl]undecanedioic Acid As described in Example 1e, starting with 3,6,9-triaza-3,6,9-tris(tert-butoxycarbonylmethyl)-5-[4-(3-(maleimido)propoxy)benzyl]undecanedioic acid bis(tert-butyl)diester (Example c), the free penta acid is obtained in a 96% yield as a white powder.
Melting point: 285° C. (decomposition).
Analysis
Calcd: C 52.82; H 5.69; N 8.80; O 32.67.
Found: C 52.70; H 5.82; N 8.74.
Gadolinium Complex
As already described in Example 1e, the gadolinium complex is obtained in quantitative yield.
Analysis
Calcd: C 42.52; H 4.20; N 7.08; O 26.30; Gd 19.88.
Found: C 42.39; H 4.21; N 7.19; Gd 19.55.
Gd (AAS): 18.63%.
Analogously to the directions given in 1e, the following salts are obtained:
Sodium Salt of the Gadolinium Complex
Analysis
Calcd: C 40.28; H 3.74; N 6.71; O 24.91; Gd 18.23; Na 5.50.
Found: C 40.18; H 3.87; N 6.69; Gd 18.68; Na 5.57.
Meglumine Salt of the Gadolinium Complex
Analysis
Calcd: C 42.70; H 5.85; N 7.28; O 30.52; Gd 13.63.
Found: C 42.60; H 5.70; N 7.36; Gd 13.61.
Morpholine Salt of the Gadolinium Complex
Analysis
Calcd: C 44.89; H 5.12; N 8.72; O 24.91; Gd 16.32.
Found: C 44.90; H 5.11; N 8.63; Gd 15.98.
The following are obtained analogously to the directions for preparing the gadolinium complex:
Indium Complex
Calcd: C 44.93; H 4.44; N 7.49; O 27.79; In 15.34.
Found: C 44.99; H 4.50; N 7.38; In 15.41.
Yttrium Complex
Calcd: C 45.48; H 4.59; N 7.75; O 28.75; Y 12.43.
Found: C 46.46; H 4.48; N 7.58; Y 12.15.
Ytterbium Complex
Calcd: C 41.68; H 4.12; N 6.95; O 25.79; Yb 21.45.
Found: C 41.75; H 4.08; N 6.92; Yb 21.32.
Samarium Complex
Calcd: C 42.89; H 4.24; N 7.15; O 26.53; Sm 19.18.
Found: C 42.88; H 4.36; N 7.22; Sm 19.15.
Praseodymium Complex
Calcd: C 43.42; H 4.29; N 7.24; O 26.86; Pr 18.19.
Found: C 43.43; H 4.24; N 7.30; Pr 18.32.
Cobalt Complex
Calcd: C 48.56; H 4.80; N 8.09; O 30.04; Co 8.51.
Found: C 48.55; H 4.49; N 8.12; Co 8.55.

EXAMPLE 19

(a) 3,6,9-Triaza-3,6,9-tris(tert-butoxycarbonylmethyl)-5-(4-hydrazinocarbonylmethoxybenzyl)undecanedioic Acid Bis(tert-butyl)diester With the directions given in Example 4a, 15.2 g (13.57 mmol) of 3,6,9-triaza-5-(4-benzyloxycarbonylmethoxybenzyl)-3,6,9-tris(tert-butoxycarbonylmethyl)undecanedioic acid bis(tert-butyl) diester (Example 17e) yields 9.6 g (83% of theory) of an oil that is highly viscous at room temperature.
Analysis
Calcd: C 60.61; H 8.63; N 8.21; O 22.53.
Found: C 60.49; H 8.52; N 8.23.

(b) 3,6,9-Triaza-3,6,9-tris(carboxymethyl)-5-(4-hydrazinocarbonylmethoxybenzyl)undecanedioic Acid According to the method disclosed in Example 4b, 2.1 g (7.9 mmol) of 3,6,9-triaza-3,6,9-tris-(tert-butoxycarbonylmethyl)-5-(4-hydrazinocarbonylmethoxybenzyl)undecanedioic acid bis (tert-butyl)diester (Example a) is reacted with trifluoroacetic acid. After the reaction mixture has been worked up, 3.1 g of white crystals (67% of theory) is obtained.
Melting point: 180° C. (decomposition).
Analysis
Calcd: C 48.33; H 5.81 B 12.25; O 33.59.
Found: C 48.15; H 5.83; N 12.31.
The gadolinium complex was prepared using the procedure described in Example 1e.
Analysis
Calcd: C 33.06; H 4.16; N 9.64; O 26.45; Gd 21.66.
Found: C 32.97; H 4.17; N 9.70; Gd 21.65.
Gd (AAS): 21.63%.
The following salts are obtained analogously to the directions given in 1e:
Sodium Salt of the Gadolinium Complex
Analysis
Calcd: C 35.88; H 3.66; N 9.09; O 24.94; Gd 20.42; Na 5.97.
Found: C 35.76; H 3.68; N 9.11; Gd 20.19; Na 6.00.
Meglumine Salt of the Gadolinium Complex
Analysis
Calcd: C 39.85; H 5.69; N 8.79; O 31.56; Gd 14.10.
Found: C 39.80; H 5.72; N 8.71; Gd 14.02.
Morpholine Salt of the Gadolinium Complex
Analysis
Calcd: C 41.46; H 5.16; N 10.91; O 24.94; Gd 17.51.
Found: C 41.51; H 5.15; N 10.78; Gd 17.36.

EXAMPLE 20

(a) 3,6,9-Triaza-3,6,9-tris(tert-butoxycarbonylmethyl)-5-(4-benzyloxycarbonylpentamethylenoxybenzyl)undecanedioic Acid Bis(tert-butyl)diester According to the directions given for Example 3a, 3.8 g (4.87 mmol) of 3,6,9-triaza-3,6,9-tris(tert-butoxycarbonylmethyl)-5-(4-hydroxybenzyl)undecanedioic acid bis(tert-butyl)diester (Example 17d) yields 3.69 g (77% of theory) of a colorless oil.

Analysis

Calcd: C 65.89; H 8.70; N 4.26; O 21.13.

Found: C 65.66; H 8.63; N 4.38.

(b) 3,6,9-Triaza-3,6,9-tris(carboxymethyl)-5-(4-benzyloxycarbonylpentamethylenoxybenzyl) undecanedioic Acid According to the method set forth in Example 3b, 8.3 g (8.43 mmol) of 3,6,9-triaza-3,6,9-tris(tert-butoxycarbonylmethyl)-5-(4-benzyloxycarbonylpentamethylenoxybenzyl)undecanedioic acid bis(tert-butyl)diester (Example a) yields 5.51 g (93% of theory) of a white crystallized product.

Melting point: 183° C. (decomposition).

Analysis

Calcd: C 58.02; H 6.44; N 5.97; O 29.55.

Found: C 58.09; H 6.31; N 6.03.

Gadolinium Complex

According to the method disclosed in Example 1e, the gadolinium complex is obtained in an almost quantitative yield.

Analysis

Calcd: C 47.59; H 4.93; N 4.89; O 24.24; Gd 18.32.

Found: C 47.70; H 4.70; N 4.82; Gd 18.50.

Analogously to the directions given in 1e, the following salts are obtained:

Sodium Salt of the Gadolinium Complex

Analysis

Calcd: C 45.27; H 4.47; N 4.65; O 23.06; Gd 17.43; Na 5.09.

Found: C 45.30; H 4.48; N 4.62; Gd 17.28; Na 5.01.

Meglumine salt of the Gadolinium Complex

Analysis

Calcd: C 6.18; H 6.13; N 5.60; O 29.47; Gd 12.59.

Found: C 46.19; H 6.09; N 5.71; Gd 12.52.

Morpholine Salt of the Gadolinium Complex

Analysis

Calcd: C 48.96; H 5.67; N 6.79; O 23.29; Gd 15.26.

Found: C 49.03; H 5.66; N 6.80; Gd 15.11.

EXAMPLE 21

(a) 3,6,9-Triaza-3,6,9-tris(tert-butoxycarbonylmethyl)-5-(4-hydrazinocarbonylpentamethylenoxybenzyl) undecanedioic Acid Bis(tert-butyl)diester According to the directions given for Example 4a, 13.05 g (13.26 mmol) of 3,6,9-triaza-3,6,9-tris(tert-butoxycarbonylmethyl)-5-(4-benzyloxycarbonylpentamethylenoxybenzyl)undecanedioic acid bis(tert-butyl)diester (Example 20a) yields 10.72 g (89% of theory) of a colorless oil.

Analysis

Calcd: C 62.25; H 8.99; N 7.71; O 21.14.

Found: C 62.16; N 9.01; N 7.75.

(b) 3,6,9-Triaza-3,6,9-tris(carboxymethyl)-5-(4-hydrazinocarbonylpentamethylenoxybenzyl) undecanedioic Acid According to the directions given for Example 4b, 4.5 g (4.95 mmol) of 3,6,9-triaza-3,6,9-tris(tert-butoxycarbonylmethyl)-5-(4-hydrazinocarbonylpentamethylenoxybenzyl)undecanedioic acid bis(tert-butyl)diester (Example a) yields 2.80 g (90% of theory) of a white crystallized product.

Melting point: 217° C. (decomposition).

Analysis

Calcd: C 51.66; H 6.58; N 11.15; O 30.58.

Found: C 51.49; H 6.55; N 11.12.

Gadolinium Complex

In accordance with the method disclosed in Example 1e, the gadolinium complex is obtained in an almost quantitative yield.

Analysis

Calcd: C 41.47; H 4.89; N 8.95; O 24.55; Gd 20.11.

Found: C 41.50; H 4.85; N 8.80; Gd 20.01.

The following salts are obtained in analogy to the directions given in 1e:

Sodium Salt of the Gadolinium Complex

Analysis

Calcd: C 39.26; H 4.39; N 8.48; O 23.24; Gd 19.04; Na 5.56.

Found: C 39.18; H 4.33; N 8.40; Gd 19.00; Na 5.53.

Meglumine Salt of the Gadolinium Complex

Analysis

Calcd: C 42.00; H 6.19; N 8.36; O 30.02; Gd 13.41.

Found: C 42.10; H 6.15; N 8.33; Gd 13.20.

Morpholine Salt of the Gadolinium Complex

Analysis

Calcd: C 44.06; H 5.70; N 10.27; O 23.47; Gd 16.48.

Found: C 43.95; H 5.71; N 10.23; Gd 16.42.

EXAMPLE 22

(a) 3,6,9-Triaza-3,6,9-tris(tert-butoxycarbonylmethyl)-5-[4-(methacryloyl) hydrazinocarbonylpentamethylenoxybenzyl] undecanedioic Acid Bis(tert-butyl)diester According to the directions given for Example 7a, 9.0 g (9.9 mmol) of 3,6,9-triaza-3,6,9-tris(tert-butoxycarbonylmethyl)-5-(4-hydrazinocarbonylpentamethylenoxybenzyl)undecanedioic acid bis° (tert-butyl)diester (Example 21a) yields 6.58 g (68% of theory) of a colorless oil.

Analysis

Calcd: C 62.74; H 8.77; N 7.17; O 21.3.

Found: C 62.63; H 8.72; N 7.21.

(b) 3,6,9-Triaza-3,6,9-tris(carboxymethyl)-5-[4-(methacryloyl) hydrazinocarbonylpentamethylenoxybenzyl] undecanedioic Acid According to the method set forth in Example 3b, 2.25 g (2.3 mmol) of 3,6,9-triaza-3,6,9-tris(tert-butoxycarbonylmethyl)-5-[4-(methacryloyl)-hydrazinocarbonylpentamethylenoxybenzyl)undecanedioic acid bis(tert-butyl)diester (Example a) yields 1.41 g (88% of theory) of a white crystallized product.

Melting point: 139° C. (decomposition).

Analysis

Calcd: C 53.51; H 6.51; N 10.06; O 29.89.

Found: C 53.52; H 6.50; N 10.13.

Gadolinium Complex

According to the method described in Example 1e, the gadolinium complex is obtained in an almost quantitative yield.

Analysis
Calcd: C 43.80; H 4.98; N 8.23; O 24.47; Gd 18.50.
Found: C 43.71; H 4.86; N 8.31; Gd 18.38.

Analogously to the directions given in 1e, the following salts are obtained:
Sodium Salt of the Gadolinium Complex
Analysis
Calcd: C 41.60; H 4.61; N 7.82; O 23.24; Gd 17.57; Na 5.13.
Found: C 41.61; H 4.58; N 7.80; Gd 17.39; Na 5.08.
Meglumine Salt of the Gadolinium Complex
Analysis
Calcd: C 43.53; H 6.25; N 7.89; O 29.64; Gd 12.66.
Found: C 43.53; H 6.20; N 7.88; Gd 12.45.
Morpholine Salt of the Gadolinium Complex
Analysis
Calcd: C 45.78; H 5.81; N 9.58; O 23.45; Gd 15.36.
Found: C 45.79; H 5.77; N 9.55; Gd 15.20.

EXAMPLE 23

(a) 3,6,9-Triaza-3,6,9-tris(tert-butoxycarbonylmethyl)-5-[4-(3-(methacrylamido)propoxy)benzyl]undecanedioic Acid Bis(tert-butyl) diester According to the method described in Example 2a, starting with 3,6,9-triaza-3,6,9-tris-(tert-butoxycarbonylmethyl)-5-[4-(3-aminopropoxy)benzyl]undecanedioic acid bis(tert-butyl)diester (Example 18b), the title compound is obtained in an 86% yield as an oil.

Analysis
Calcd: C 63.69; H 8.90; N 6.18; O 21.21.
Found: C 63.80; H 8.74; N 6.25.

(b) 3,6,9-Triaza-3,6,9-tris(carboxymethyl)-5-[4-(3-(methacrylamido)propoxy)benzyl]undecanedioic Acid Starting with 3,6,9-triaza-tris(tert-butoxycarbonylmethyl)-5-[4-(3-(methacrylamido)propoxy)benzyl]undecanedioic acid bis(tert-butyl)diester (Example a), the title compound is obtained in a 91% yield in analogy to the procedure disclosed in Example 2b.

Analysis
Calcd: C 53.83; H 6.45; N 8.96; O 30.73.
Found: C 53.78; H 6.31; N 8.95.
Gadolinium Complex
Analogously to the directions in Example 1e, the gadolinium complex is obtained in a 98% yield.
Analysis
Calcd: C 43.17; H 4.78; N 7.19; O 24.65; Gd 20.18.
Found: C 43.33; H 4.60; N 7.15; Gd 20.12.
Gd (AAS); 20.23%

Analogously to the directions given in 1e, the following salts are obtained:
Sodium Salt of the Gadolinium Complex
Analysis
Calcd: C 40.87; H 4.28; N 6.80; O 23.33; Gd 19.11; Na 5.58.
Found: C 40.88; H 4.25; N 6.78; Gd 19.05; Na 5.59.
Meglumine Salt of the Gadolinium Complex
Analysis
Calcd: C 43.10; H 6.20; N 7.18; O 30.07; Gd 13.43.
Found: C 43.01; H 6.15; N 7.14; Gd 13.40.
Morpholine Salt of the Gadolinium Complex
Analysis
Calcd: C 45.41; H 5.71; N 8.82; O 23.52; Gd 16.51.
Found: C 45.38; H 5.77; N 8.80; Gd 16.41.

EXAMPLE 24

(a) 3,6,9-Triaza-3,6,9-tris(tert-butoxycarbonylmethyl)-5-(4-carboxymethoxybenzyl)undecanedioic Acid Bis (tert-butyl)diester In accordance with the directions set forth in Example 8a, 4.9 g (5.16 mmol) of 3,6,9-triaza-5-(4-benzyloxycarbonylmethoxybenzyl)-3,6,9-tris(tert-butoxycaronylmethyl)undecanedioic acid bis(tert-butyl) diester (Example 17e) yields 4.1 g of a colorless, viscous oil (93.2% of theory).

Analysis
Calcd: C 61.62; H 8.53; N 5.01; O 24.81.
Found: C 61.66; H 8.45; N 5.15.

(b) 3,6,9-Triaza-3,6,9-tris(tert-butoxycarbonylmethyl)-5-[4-[(2,3,4,5,6-pentahydroxyhexyl)-methylamino]carbonylmethoxybenzyl]undecanedioic Acid Bis (tert-butyl)diester 3.90 g (4.6 mmol) of 3,6,9-triaza-3,6,9-tris(tert-butoxycarbonylmethyl)-5-(4-carboxymethoxybenzyl)undecanedioic acid bis(tert-butyl)diester is dissolved in 80 ml of tetrahydrofuran and combined with 0.43 g (6.8 mmol) of triethylamine. At −5° C., 0.62 g (4.70 mmol) of chloroformic acid isobutyl ester in 30 ml of tetrahydrofuran is gently added, and the mixture is finally combined with 10 ml of an aqueous solution of 920 mg (4.7 mmol) of N-methyl-D-glucamine. After 30 minutes of agitation at 0° C., the cooling bath is removed and the mixture allowed to warm up to room temperature. After evaporation of the solvent, the residue is purified by chromatography on silica gel, thus obtaining 3.73 g of a white crystalline compound (80% of theory), decomposing with brown discoloration starting at 50° C.

Analysis
Calcd: C 59.15; H 8.53; N 5.51; O 26.79.
Found: C 59.18; H 8.60; N 5.55.

(c) 3,6,9-Triaza-3,6,9-tris (carboxymethyl)-5-[4-[(2,3,4,5,6-pentahydroxyhexyl)methylamino]carbonylmethoxybenzyl]undecanedioic Acid As described in Example 1e, 1.77 g (1.7 mmol) of 3,6,9-triaza-3,6,9-tris(tert-butoxycarbonylmethyl)-5-[4-[(2,3,4,5,6-pentahydroxyhexyl)methylamino]carbonylmethoxybenzyl]undecanedioic acid bis(tert-butyl) diester yields 1.04 g (83% of theory) of the title compound, melting point 132° C. (decomposition).

Analysis
Calcd: C 49.04; H 6.31; N 7.62; O 37.01.
Found: C 49.12; H 6.35; N 7.50.
Gadolinium Complex
Analogously to the directions in Example 1e, the gadolinium complex is obtained in a 98% yield.
Analysis
Calcd: C 40.53; H 4.87; N 6.30; O 30.59; Gd 17.68.
Found: C 40.61; H 4.71; N 6.35; Gd 17.92.
Gd (AAS): 17.86% by weight.

The following salts are obtained analogously to the directions given in 1e:

Sodium Salt of the Gadolinium Complex
Analysis
Calcd: C 38.62; H 4.42; N 6.00; O 29.15; Gd 16.85; Na 4.92.
Found: C 38.57; H 4.43; N 6.03; Gd 16.54; Na 4.88.
Meglumine Salt of the Gadolinium Complex
Analysis
Calcd: C 41.30; H 6.06; N 6.56; O 33.76; Gd 12.29.
Found: C 41.17; H 5.98; N 6.59; Gd 11.97.
Morpholine Salt of the Gadolinium Complex
Analysis
Calcd: C 43.01; H 5.60; N 7.91; O 28.64; Gd 14.81.
Found: C 42.96; H 5.52; N 7.97; Gd 14.85.

EXAMPLE 25

(a) 3,6-Diaza-3,6-bis(tert-butoxycarbonylmethyl)-4-[4-(2-propynyloxy)benzyl]suberic Acid Bis(tert-butyl)diester In succession, a solution of 3.77 g (6.05 mmol) of 3,6-diaza-3,6-bis(tert-butoxycarbonylmethyl)-4-(4-hydroxybenzyl) suberic acid bis(tert-butyl)diester (Example 1a) in 20 ml of toluene and a solution of 750 mg (6.3 mmol) of 3-bromopropyne in 20 ml of toluene are added dropwise to a suspension of 390 mg of sodium hydride (80% in paraffin)(13.3 mmol) in 50 ml of toluene. After 2 hours, the mixture is filtered, washed with water, and chromatographed on silica gel after evaporation, thus obtaining 3.02 g of an oil (75.5% of theory).
Analysis
Calcd: C 65.43; H 8.54; N 4.23; O 21.78.
Found: C 65.33; H 8.60; N 4.30.

(b) 3,6-Diaza-3,6-bis(carboxymethyl)-4-[4-(2-propynyloxy)benzyl]suberic Acid

According to the directions given for Example 1e, 1.35 g (2 mmol) of 3,6-diaza-3,6-bis(tert-butoxycarbonylmethyl)-4-[4-(2-propynyloxy)benzyl]suberic acid bis(tert-butyl) diester is reacted, thus obtaining a white powder (740 mg, 83% of theory) melting at 140° C. with decomposition.
Analysis
Calcd: C 55.04; H 5.54; N 6.41; O 32.99.
Found: C 55.13; H 5.59; N 6.40.
Gadolinium Complex
The gadolinium complex is obtained as described in 1e.
Analysis
Calcd: C 40.67; H 3.58; N 4.74; O 24.37; Gd 26.62.
Found: C 40.80; H 3.60; N 4.70; Gd 26.36.
The following salts are obtained analogously to the directions given in 1e:
Sodium Salt of the Gadolinium Complex
Analysis
Calcd: C 39.21; H 3.29; N 4.57; O 23.50; Gd 25.66; Na 3.75.
Found: C 39.22; H 3.22; N 4.60; Gd 25.36; Na 3.74.
Meglumine Salt of the Gadolinium Complex
Analysis
Calcd: C 41.26; H 4.87; N 5.34; O 28.50; Gd 20.00.
Found: C 41.22; H 4.89; N 5.32; Gd 20.31.
Morpholine Salt of the Gadolinium Complex
Analysis
Calcd: C 42.59; H 4.31; N 6.20; O 23.64; Gd 23.23.
Found: C 42.48; H 4.30; N 6.15; Gd 23.15.

EXAMPLE 26

(a) 3,6,9-Triaza-3,6,9-tris(tert-butoxycarbonylmethyl)-4-[4-(2-propynyloxy)benzyl] undecanedioic Acid Bis(tert-butyl)diester 5.36 g (6.87 mmol) of 3,6,9-triaza-3,6,9-tris(tert-butoxycarbonylmethyl)-4-(4-hydroxybenzyl)undecanedioic acid bis(tert-butyl)diester (Example 9f) is dissolved in 70 ml of toluene and gently combined with 363 mg of sodium hydride (15.1 mmol). To this mixture is added dropwise 858 mg of 3-bromopropyne (7.2 mmol) in 30 ml of toluene.

After 2 hours, the solution is filtered, the organic phase is washed twice with water, and the solvent is removed. After chromatography on silica gel, 4.89 g of a colorless oil is obtained (87% of theory).
Analysis
Calcd: C 64.60; H 8.74; N 5.13; O 21.51.
Found: C 64.57; H 8.64; N 5.15.

(b) 3,6,9-Triaza-3,6,9-tris(carboxymethyl)-4-[4-(2-propynyloxy)benzyl]undecanedioic Acid In accordance with the directions given for Example 1e, 4.35 g (5.32 mmol) of 3,6,9-triaza-3,6,9-tris(tert-butoxycarbonylmethyl)-4-[4-(2-propynyloxy)benzyl] undecanedioic acid bis(tert-butyl)diester is reacted, thus obtaining a white powder (2.42 mg, 85% of theory) melting at 142° C. with decomposition.
Analysis
Calcd: C 53.62; H 5.81; N 7.81; O 32.74.
Found: C 53.66; H 5.85; N 7.82.
Gadolinium Complex
The gadolinium complex is obtained as described in 1e.
Analysis
Calcd: C 41.67; H 4.07; N 6.07; O 25.44; Gd 22.73.
Found: C 41.42; H 4.12; N 6.27; Gd 22.59.
In analogy with the directions given in 1e, the following salts are obtained:
Sodium Salt of the Gadolinium Complex
Analysis
Calcd: C 39.18; H 3.56; N 5.71; O 23.92; Gd 21.37; Na 6.24.
Found: C 38.97; H 3.55; N 5.65; O 23.90; Gd 21.53; Na 6.25.
Meglumine Salt of the Gadolinium Complex
Analysis
Calcd: C 42.17; H 5.77; N 6.47; O 31.04; Gd 14.53.
Found: C 42.01; H 5.63; N 6.50; O 30.98; Gd 14.55.
Morpholine Salt of the Gadolinium Complex
Analysis
Calcd: C 44.48; H 5.13; N 8.10; O 24.07; Gd 18.20.
Found: C 44.51; H 5.08; N 8.12; O 24.10; Gd 18.07.

EXAMPLE 27

(a) 3,6,9-Triaza-3,6,9-tris(tert-butoxycarbonylmethyl)-5-[4-(2-propynyloxy)benzyl] undecanedioic Acid Bis(tert-butyl)diester 4.57 g (5.8 mmol) of 3,6,9-triaza-3,6,9-tris(tert-butoxycarbonylmethyl)-5-(4-hydroxybenzyl)undecanedioic acid bis(tert-butyl)diester (Example 17d) is reacted, as described for Example 26a, with 310 mg of sodium hydride and 730 mg of 3-bromopropyne to yield the title compound. The title compound is obtained as a colorless oil with a yield of 4.07 g (74% of theory).
Analysis
Calcd: C 64.60; H 8.74; N 5.13; O 21.51
Found: C 64.64; H 8.70; N 5.20

(b) 3,6,9-Triaza-3,6,9-tris (carboxymethyl)-5-[4-(2-propynyloxy) benzyl]undecanedioic Acid 4.69 g (5.7 mmol) of 3,6,9-triaza-3,6,9-tris(tert-butoxycarbonylmethyl)-5-[4-(2-propynyloxy)benzyl]

undecanedioic acid bis(tert-butyl)diester is reacted in accordance with the direction given for Example 1e, thus obtaining a white powder melting at 135° C. with decomposition.

Analysis

Calcd: C 53.62; H 5.81; N 7.81; O 32.74

Found: C 53.66; H 5.90; N 7.75

Gadolinium Complex

The gadolinium complex is obtained as disclosed in 1e.

Analysis

Calcd: C 41.67; H 4.07; N 6.07; O 25.44; Gd 22.73.

Found: C 41.66; H 4.11; N 6.04; Gd 22.51.

The following salts are obtained in analogy to the method described in 1e:

Sodium Salt of the Gadolinium Complex

Analysis

Calcd: C 39.18; H 3.56; N 5.71; O 23.92; Gd 21.37; Na 6.24.

Found: C 39.32; H 3.55; N 5.80; O 23.81; Gd 21.50; Na 6.27.

Meglumine Salt of the Gadolinium Complex

Analysis

Calcd: C 42.17; H 5.77; N 6.47; O 31.04; Gd 14.53.

Found: C 42.15; H 5.60; N 6.51; O 31.05; Gd 14.37.

Morpholine Salt of the Gadolinium Complex

Analysis

Calcd: C 44.48; H 5.13; N 8.10; O 24.07; Gd 18.20.

Found: C 44.45; H 5.15; N 8.11; O 24.17; Gd 18.19.

EXAMPLE 28

(a) 11-[4-[N,N,N',N'-Tetrakis(tert-butoxycarbonylmethyl)-2,3-diaminopropyl]phenoxyacetyl]aminoundecanoic Acid [2-(tert-Butoxycarbonyl)hydrazide]

Under continuous cooling to below 5° C., 30 ml of a solution of 3.65 g (26.8 mmol) of chloroformic acid isobutyl ester in tetrahydrofuran is added dropwise to a solution of 18.23 g (26.78 mmol) of 3,6-diaza-3,6-bis(tert-butoxycarbonylmethyl)-4-(4-carboxymethoxybenzyl) suberic acid bis(tert-butyl)diester (Example 8a) and 2.7 g (26.8 mmol) of triethylamine in 200 ml of dry tetrahydrofuran. Half an hour after completion of this addition, during which time cooling and agitation are continued, a solution of 8.44 g (26.8 mmol) of 11-aminoundecanoic acid 2-(tert-butoxycarbonyl)hydrazide is added gradually thereto. Then the mixture is allowed to warm up to room temperature under agitation and the solvent is evaporated. The residue is taken up in 400 ml of toluene, and water-soluble proportions are extracted with saturated sodium chloride solution. After washing with water and drying, the solvent is evaporated and the oil is subjected to purification by chromatography on silica gel, yielding 20.1 g (79% of theory) of a colorless oil.

Analysis

Calcd: C 63.19; H 9.22; N 7.36; O 20.2.

Found: C 63.17; H 9.25; N 7.31.

(b) 11-[4-[N,N,N',N'-Tetrakis(carboxymethyl)-2,3-diaminopropyl]phenoxyacetyl]aminoundecanoic Acid Hydrazide As described for Example 1e, the tert-butyl esters can be split off with trifluoroacetic acid at room temperature. Under these conditions, in case of 11-[4-[N,N,N',N'-tetrakis(tert-butoxycarbonylmethyl)-2,3-diaminopropyl]phenoxyacetyl] aminoundecanoic acid [2-(tert-butoxycarbonyl)hydrazide], the tert-butoxycarbonyl blocking group of the acid hydrazide is likewise split off, thus obtaining, using the procedure described in Example 1e, from 12.56 g of starting material (13.2 mmol) in a 77.3% yield 6.68 g of a white crystalline compound which begins to melt at 115° C. under decomposition.

Analysis

Calcd: C 55.11; H 7.24; N 10.71; O 26.92.

Found: C 54.98; H 7.30; N 10.77.

Gadolinium Complex

Analysis

Calcd: C 44.59; H 5.48; N 8.66; O 21.78; Gd 19.46.

Found: C 44.55; H 5.49; N 8.71; Gd 19.21.

Analogously to the directions given in 1e, the following salts are obtained:

Sodium Salt of the Gadolinium Complex

Analysis

Calcd: C 43.41; H 5.22; N 8.43; O 21.20; Gd 18.94; Na 2.77.

Found: C 43.36; H 5.19; N 8.47; Gd 18.59; Na 2.76.

Meglumine Salt of the Gadolinium Complex

Analysis

Calcd: C 44.30; H 6.12; N 8.57; O 25.51; Gd 15.67.

Found: C 44.33; H 6.15; N 8.51; Gd 15.76.

Morpholine Salt of the Gadolinium Complex

Analysis

Calcd: C 45.67; H 5.86; N 9.39; O 21.47; Gd 17.58.

Found: C 45.77; H 5.80; N 9.28; Gd 17.38.

EXAMPLE 29

(a) 11-[[4-[4-(tert-Butoxycarbonylmethyl)]-4-aza-2,6-di[bis(tert-butoxycarbonylmethyl)amino]hexyl]-phenoxyacetyl]aminoundecanoic Acid [2-(tert-Butoxycarbonyl)hydrazide]

8.4 g (10 mmol) of 3,6,9-triaza-3,6,9-tris-(tert-butoxycarbonylmethyl)-4-(4-carboxymethoxybenzyl)-undecanoic acid bis(tert-butyl)diester (Example 16a) is reacted according to the directions for Example 28a with the equivalent amounts of triethylamine, chloroformic acid isobutyl ester and 11-aminoundecanoic acid 2-(tert-butoxycarbonyl)hydrazide. After purification by column chromatography, 8.74 g (77% of theory) of a colorless oil is produced.

Analysis

Calcd: C 62.40; H 9.05; N 7.40; O 21.13.

Found: C 62.31; H 9.10; N 7.36.

(b) 11-[4-[4-(Carboxymethyl)-4-aza-2,6-di[bis(carboxymethyl)amino]hexyl]phenoxyacetyl] aminoundecanoic Acid Hydrazide As described for Examples 1e and 28b, 6.32 g (5.6 mmol) of 11-[4-[4-(tert-butoxycarbonylmethyl)-4-aza-2,6-di[bis(tert-butoxycarbonylmethyl)amino]hexyl]-phenoxyacetyl] aminoundecanoic acid[2-(tert-butoxycarbonyl)hydrazide] yields, in a 76% yield, the title compound in the form of colorless crystals.

Melting point: 185° C. (decomposition).

Analysis

Calcd: C 54.10; H 7.21; N 11.13; O 27.55.

Found: C 53.98; H 7.23; N 11.10.

Gadolinium Complex

Analysis

Calcd: C 44.92; H 5.65; N 9.24; O 22.87; Gd 17.29.

Found: C 44.95; H 5.60; N 9.26; Gd 17.33.

The following salts are obtained analogously to the directions given in 1e:

Sodium Salt of the Gadolinium Complex

Analysis

Calcd: C 42.85; H 5.18; N 8.81; O 21.82; Gd 16.50; Na 4.82.

Found: C 42.69; H 5.12; N 8.80; Gd 16.25; Na 4.83.

Meglumine Salt of the Gadolinium Complex

Analysis

Calcd: C 44.36; H 6.59; N 8.62; O 28.31; Gd 12.10.

Found: C 44.35; H 6.50; N 8.63; Gd 12.15.

Morpholine Salt of the Gadolinium Complex

Analysis

Calcd: C 46.65; H 6.24; N 10.36; O 22.19; Gd 15.54.

Found: C 46.66; H 6.30; N 10.24; Gd 15.32.

EXAMPLE 30

(a) 11-[4-[3-[(tert-Butoxycarbonylmethyl)-3-aza]-2-[[bis(tert-butoxycarbonylmethyl)amino]methyl]-5-[bis(tert-butoxycarbonylmethyl)amino]pentyl]-5 phenoxyacetyl]aminoundecanoic Acid [2-(tert-Butoxycarbonyl)hydrazide]

According to the directions for Example 28a, 6.13 g (7.3 mmol) of 3,6,9-triaza-3,6,9-tris(tert-butoxycarbonylmethyl)-5-(4-carboxymethoxybenzyl)undecanoic acid bis(tert-butyl)diester (Example 24a) is reacted with equivalent amounts of triethylamine, chloroformic acid isobutyl ester, and 11-aminoundecanoic acid 2-(tert-butoxycarbonyl) hydrazide. After purification by column chromatography, 7.04 g (85% of theory) of a colorless oil is produced.

Analysis

Calcd: C 62.4; H 9.05; N 7.40; O 21.13.

Found: C 62.31; H 9.17; N 7.56.

(b) 11-[4-[3-[(Carboxymethyl)-3-aza]-2-[[bis(carboxymethyl)amino]methyl]-5-[bis(carboxymethyl)amino]-pentyl]phenoxyacetyl]aminoundecanoic Acid Hydrazide In accordance with the procedure described for Examples 1e and 28b, 5.38 g (4.7 mmol) of 11-[4-[3-[(tert-butoxycarbonylmethyl)-3-aza]-2-[[bis(tert-butoxycarbonylmethyl)amino]methyl]-5-[bis(tert-butoxycarbonylmethyl)amino]pentyl]phenoxyacetyl] aminoundecanoic acid [2-(tert-butoxycarbonyl)hydrazide] yields 2.93 g (82% of theory) of colorless crystals.

Melting point: 192° (decomposition).

Analysis

Calcd: C 54.1; H 7.21; N 11.13; O 27.55.

Found: C 54.09; H 7.28; N 11.11.

Gadolinium Complex

Analysis

Calcd: C 44.92; H 5.65; N 9.24; O 22.87; Gd 17.29.

Found: C 44.80; H 5.66; N 9.22; Gd 17.03.

Analogously to the directions indicated in 1e, the following salts are obtained:

Sodium Salt of the Gadolinium Complex

Analysis

Calcd: C 42.85; H 5.18; N 8.81; O 21.82; Gd 16.50; Na 4.82.

Found: C 42.88; H 5.12; N 8.83; Gd 16.91; Na 4.88.

Meglumine Salt of the Gadolinium Complex

Analysis

Calcd: C 44.36; H 6.59; N 8.62; O 28.31; Gd 12.10.

Found: C 44.32; H 6.30; N 8.71; Gd 12.12.

Morpholine Salt of the Gadolinium Complex

Analysis

Calcd: 46.65; H 6.24; N 10.36; O 22.19; Gd 15.54.

Found: C 46.39; H 6.26; N 10.32; Gd 15.61.

EXAMPLE 31

(a) 3,6-Diaza-3,6-bis(tert-butoxycarbonylmethyl)-4-(4-oxiranylmethoxy)benzylsuberic Acid Bis(tert-butyl)diester 17.38 g (27.9 mmol) of 3,6-diaza-3,6-bis(tert-butoxycarbonylmethyl)-4-(4-hydroxybenzyl)suberic acid bis(tert-butyl)diester (Example 1a) is dissolved with 900 mg (3 mmol) of 80% sodium hydride in paraffin under agitation in 300 ml of toluene and, at 40° C., combined dropwise with a solution of 2.6 g (28 mmol) of epichlorohydrin. After one hour, the mixture is gently combined with 100 ml of water. After shaking, the phases are separated and then the organic phase is concentrated after drying. Chromatographic purification yields 15.5 g (22.8 mmol, 82% of theory) of a colorless oil.

Analysis

Calcd: C 63.69; H 8.61; N 4.12; O 23.56.

Found: C 63.57; H 8.62; N 4.07.

(b) 15-[4-[N,N,N',N'-Tetrakis(tert-butoxycarbonylmethyl)-2,3-diaminopropyl]phenoxy]-12-aza-14-hydroxypentadecanoic Acid 2-(Butoxycarbonyl)hydrazide 7.35 g (10.8 mmol) of 3,6-diaza-3,6-bis(tert-butoxycarbonylmethyl)-4-(4-oxiranylmethoxy) benzylsuberic acid bis(tert-butyl)diester, dissolved in 100 ml of diethyl ether, is combined with 3.41 g (10.8 mmol) of 11-aminoundecanoic acid 2-(tert-butoxycarbonyl)hydrazide in 100 ml of tetrahydrofuran, and heated to reflux for 2 hours. After evaporation of the solvent, the compound is obtained analytically pure as a colorless oil.

Yield: 9.54 g (88.5% of theory).

Analysis

Calcd: C 62.81; H 9.22; N 7.04; O 20.91.

Found: C 62.65; H 9.23; N 7.15.

(c) 15-[4-[N,N,N',N'-Tetrakis(carboxymethyl)-2,3-diaminopropyl]phenoxy]-12-aza-14-hydroxypentadecanoic Acid Hydrazide 4.36 g (4.3 mmol) of 15-[4-[2,3-N,N,N',N'-tetrakis(tert-butoxycarbonylmethyl)-2,3-diaminopropyl]phenoxy]-12-aza-14-hydroxypentadecanoic acid [2-(butoxycarbonyl) hydrazide] is dissolved at room temperature in 50 ml of trifluoroacetic acid and worked up after 5 hours as described for Example 1e, yielding 2.86 g (3.2 mmol; 73% of theory) of colorless crystals.

Melting point: 145° C. (decomposition).

Analysis

Calcd: C 55.59; H 7.62; N 10.45; O 26.27.

Found: C 55.60; H 7.49; N 10.55.

Gadolinium Complex

Calcd: C 45.18; H 5.87; N 8.49; O 21.35; Gd 19.08.

Found: C 45.20; H 5.88; N 8.62; Gd 19.09.

Analogously to the direction given in 1e, the following salts are obtained:

Sodium Salt of the Gadolinium Complex

Analysis

Calcd: C 44.01; H 5.59; N 8.27; O 20.80; Gd 18.58; Na 2.71.
Found: C 43.95; H 5.61; N 8.23; Gd 18.38; Na 2.77.
Meglumine Salt of the Gadolinium Complex
Analysis
Calcd: C 44.82; H 6.33; N 8.25; O 28.14; Gd 15.44.
Found: C 44.69; H 6.43; N 8.20; Gd 15.40.
Morpholine Salt of the Gadolinium Complex
Analysis
Calcd: C 46.24; H 6.09; N 9.24; O 21.11; Gd 17.29.
Found: C 46.23; H 6.11; N 9.28; Gd 17.17.

EXAMPLE 32

(a) 3,6,9-Triaza-3,6,9-tris(tert-butoxycarbonylmethyl)-4-(4-oxiranylmethoxybenzyl)undecanedioic Acid Bis(tert-butyl)diester 16.35 g (21.0 mmol) of 3,6,9-triaza-3,6,9-tris(tert-butoxycarbonylmethyl)-4-(4-hydroxybenzyl)undecanedioic acid bis(tert-butyl)diester (Example 9f) is dissolved with 630 mg (21 mmol) of sodium hydride (80% in paraffin) under agitation in 300 ml of toluene and, at 40° C., combined dropwise with a solution of 1.95 g (21 mmol) of epichlorohydrin in 20 ml of toluene. After the reaction mixture has been worked up as disclosed for Example 31a, 15.4 g (88% of theory) of a colorless oil is obtained.

Analysis
Calcd: C 63.20; H 8.80; N 5.02; O 22.96.
Found: C 63.35; H 8.76; N 5.09.

(b) 15-[4-[4-Aza-2,6-diamino-N,N,N',N",N"-pentakis(tert-butoxycarbonylmethyl)hexyl]phenoxy]-12-aza-14-hydroxypentadecanoic Acid (2-tert-Butoxycarbonyl)hydrazide.

7.5 g (9.0 mmol) of 3,6,9-triaza-3,6,9-tris(tert-butoxycarbonylmethyl)-4-(4-oxiranylmethoxybenzyl)undecanedioic Acid Bis(tert-butyl)diester, dissolved in 100 ml of dry diethyl ether is combined with 2.85 g (9.0 mmol) of 11-aminoundecanoic acid (2-tert-butoxycarbonyl)hydrazide in 50 ml of dry tetrahydrofuran and heated under reflux for 2 hours. After evaporation of the solvent and chromatography on silica gel, 9.12 g (88% of theory) of a colorless oil is obtained.

Analysis
Calcd: C 62.58; H 9.27; N 7.29; O 20.84.
Found: C 62.83; H 9.30; N 7.28.

(c) 15-[4-[4-Aza-2,6-diamino-N,N,N',N",N"-pentakis(carboxymethyl)hexyl]phenoxy]-12-aza-14-hydroxypentadecanoic Acid Hydrazide As described for Example 1e, the title compound is obtained in an 80% yield in the form of white crystals having a melting point above 135° C. (decomposition).

Analysis
Calcd: C 54.53; H 7.58; N 10.90; O 26.88.
Found: C 54.62; H 7.48; N 10.88.
Gadolinium Complex
Calcd: C 45.44; H 5.99; N 9.08; O 22.48; Cd 16.99.
Found: C 45.38; H 6.02; N 9.05; Cd 16.76.
The following salts are obtained in analogy to the directions given in 1e:
Sodium Salt of the Gadolinium Complex
Analysis Calcd: C 43.38; H 5.51; N 8.67; O 21.46; Gd 16.22; Na 4.74.
Found: C 43.42; H 5.49; N 8.70; Gd 16.03; Na 4.77.
Meglumine Salt of the Gadolinium Complex
Analysis
Calcd: C 44.80; H 6.67; N 8.53; O 28.01; Gd 11.97.
Found: C 44.84; H 6.70; N 8.51; Gd 11.88.
Morpholine Salt of the Gadolinium Complex
Analysis
Calcd: C 47.15; H 6.34; N 10.23; O 21.91; Gd 14.35.
Found: C 47.14; H 6.20; N 10.25; Gd 14.50.

EXAMPLE 33

(a) 3,6,9-Triaza-3,6,9-tris(tert-butoxycarbonylmethyl)-5-(4-oxiranylmethoxybenzyl)undecanedioic Acid Bis(tert-butyl)diester Analogously to Example 32a, the title compound is produced from the compound disclosed in Example 17d in an 82% yield as a colorless oil.

Analysis
Calcd: C 63.20; H 8.80; N 5.02; O 22.96.
Found: C 63.15; H 8.69; N 4.93.

(b) 15-[4-[3-Aza-3-(tert-butoxycarbonylmethyl)-2-[[bis(tert-butoxycarbonylmethyl)amino]methyl]-5-[bis(tert-butoxycarbonylmethyl)amino]pentyl]phenoxy]-12-aza-14-hydroxypentadecanoic Acid [2-(tert-Butoxycarbonyl)hydrazide]

As described for Example 32b, the title compound is obtained in an 81% yield as a clear oil from the compound described in 33a.

Analysis
Calcd: C 62.58; H 9.27; N 7.29; O 20.84.
Found: C 62.47; H 9.30; N 7.30.

(c) 15-[4-[3-Aza-3-(carboxymethyl)-2-[[bis(carboxymethyl)amino]methyl]-5-[bis(carboxymethyl)amino]-pentyl]phenoxy]-12-aza-14-hydroxypentadecanoic Acid Hydrazide As described for Example 32c, the title compound is obtained from the compound described in 32b as a colorless oil in an 83% yield.

Analysis
Calcd: C 54.53; H 7.58; N 10.90; O 26.88.
Found: C 54.60; H 7.55; N 10.95.
Gadolinium Complex
Calcd: C 45.44; H 5.99; N 9.08; O 22.48; Gd 16.99.
Found: C 45.43; H 5.70; N 9.21; Gd 17.01.
Analogously to the procedure of 1e, the following salts are obtained:
Sodium Salt of the Gadolinium Complex
Analysis
Calcd: C 43.38; H 5.51; N 8.67; O 21.46; Gd 16.22; Na 4.74.
Found: C 43.45; H 5.30; N 8.76; Gd 15.90; Na 4.73.
Meglumine Salt of the Gadolinium Complex
Analysis
Calcd: C 44.80; H 6.67; N 8.53; O 28.01; Gd 11.97.
Found: C 44.95; H 6.66; N 8.50; Gd 11.51.

Morpholine Salt of the Gadolinium Complex
Analysis
Calcd: C 47.15; H 6.34; N 10.23; O 21.91; Gd 14.35.
Found: C 47.16; H 6.32; N 10.31; Gd 14.39.

EXAMPLE 34

(a) 3,6-Diaza-2,7-dioxo-4-(4-hydroxybenzyl)suberic Acid Diethyl Ester 23 g (96.4 mmol) of 1,2-diamino-1-(4-hydroxybenzyl) ethane dihydrochloride is stirred with 21.4 g (212 mmol) of triethylamine in 300 ml of dry tetrahydrofuran (THF) for one hour at 50° C. and thereafter, at 5°–10° C., combined dropwise with a cooled solution of oxalic acid ethyl ester chloride (28.96, 212 mmol) with 21.4 g (212 mmol) of triethylamine in 200 ml of THF. After this adding step, the mixture is stirred for another hour at room temperature, heated for 15 minutes to reflux, and the solvent evaporated. The mixture is made into a slurry in 500 ml of toluene, thoroughly washed with water, and the organic phase is concentrated again after drying. The product, analytically pure, remains in the form of colorless crystals in an 86% yield (33.9 g).

Melting point: 176° C. (decomposition).
Analysis
Calcd: C 55.73; H 6.05; N 7.64; O 30.56.
Found: C 55.61; H 6.15; N 7.63.

(b) 3,6-Diaza-2,7-dioxo-4-(4-hydroxybenzyl)suberic Acid Diamide

In accordance with the method described in Example 17B, 17.32 g (47.2 mmol) of 3,6-diaza-2,7-dioxo-4-(4-hydroxybenzyl)suberic acid diethyl ester is reacted to the amide, thus obtaining in a 98% yield 14.28 g of white crystals which melt starting with 285° C. under brown discoloration.

Analysis
Calcd: C 50.64; H 5.23; N 18.17; O 25.94.
Found: C 50.66; H 5.20; N 18.23.

(c) 3,6-Diaza-1,8-diamino-4-(4-hydroxybenzyl) octane (Hydrochloride)

6.16 g (20 mmol) of 3,6-diaza-2,7-dioxo-4-(4-hydroxybenzyl)suberic acid diamide is made into a slurry with 200 ml of absolute THF and a gradual stream of diborane (22.6 g of NaBH$_4$ and 205 ml of boron trifluoride etherate) is passed with the aid of nitrogen through the reaction mixture under agitation. The mixture is refluxed for 96 hours, half the original quantity of diborane is once more introduced, and the mixture is refluxed for another 2 days. Thereafter, the mixture is worked up as described in connection with Example 9e. The yield is 5.65 g (71% of theory) of colorless crystals decomposing starting with 90° C.

Analysis
Calcd: C 39.36; H 7.11; N 14.21; O 4.03; Cl 35.36.
Found: C 39.42; H 7.13; N 14.03; Cl 35.31.

(d) 3,6,9,12-Tetraaza-3,6,9,12-tetrakis(tert-butoxycarbonylmethyl)-7-(4-hydroxybenzyl) tetradecanedicarboxylic Acid Bis(tert-butyl)diester According to the directions given for Example 1a, 13.21 g (33.1 mmol) of 3,6-diaza-1,8-diamino-4-(4-hydroxybenzyl)octane tetrahydrochloride is reacted with 38.7 g (198.6 mmol) of bromoacetic acid tert-butyl ester and 17.2 g (204.7 mmol) of NaHCO$_3$ in 500 ml of dimethylformamide to obtain 26.11 g (84% of theory) of a colorless oil.

Analysis
Calcd: C 62.79; H 9.03; N 5.97; O 22.19.
Found: C 62.78; H 8.87; N 5.96.

(e) 3,6,9,12-Tetraaza-3,6,9,12-tetrakis(tert-butoxycarbonylmethyl)-7-[4-(3-amino) propoxybenzyl]tetradecanedicarboxylic Acid Bis (tert-butyl)diester The 4-hydroxybenzyl compound obtained according to (d) is alkylated following the directions given for 1b. The thus-obtained product (72% yield) is utilized without isolation in the subsequent reaction stage (splitting off the amine blocking group according to the procedure of 1c), thus obtaining the title compound in an 82% yield, analytically pure, as a colorless oil.

Analysis
Calcd: C 62.75; H 9.31; N 7.03; O 20.89.
Found: C 62.70; H 9.28; N 7.13.

(f) 3,6,9,12-Tetraaza-3,6,9,12-tetrakis (carboxymethyl)-7-[4-(3-amino)propoxybenzyl] tetradecanedicarboxylic Acid 2.56 g (2.5 mmol) of the ester obtained according to (e) is stirred in 30 ml of trifluoroacetic acid (anhydrous) for 2 hours at room temperature. The mixture is then poured into 300 ml of ether, suctioned off, suspended furthermore twice with respectively 100 ml of ether, and dried; there remains 1.4 g of colorless crystals (85% of theory).

Melting point: above 135° C. (decomposition).
Analysis
Calcd: C 51.13; H 6.59; N 10.64; O 31.62.
Found: C 51.25; H 6.62; N 10.50.

The gadolinium complex is obtained as indicated in 1e:
Gadolinium Complex:
Calcd: C 41.42; H 4.96; N 8.62; O 25.61 Cd 19.36.
Found: C 41.53; H 5.01; N 8.39 Cd 19.09.

Analogously to the directions in 1e, the following,salts are obtained:
Sodium Salt of the Gadolinium Complex
Analysis
Calcd: C 38.31; H 4.24; N 7.97; O 23.69; Gd 17.91; Na 7.85.
Found: C 38.25; H 4.11; N 7.56; Gd 18.05; Na 7.86.
Meglumine Salt of the Gadolinium Complex
Analysis
Calcd: C 42.11; H 6.56; N 8.01; O 32.05; Gd 11.25.
Found: C 42.25; H 6.70; N 8.09; Gd 11.13.

EXAMPLE 35

Indium Complex of the Conjugate of 3,6,9-Triaza-3,6,9-tris(carboxymethyl)-4-[4-[3-(maleimido) propoxy]benzyl]undecanedioic Acid with Fab Fragments of Monoclonal Antibody 7B10D11

(a) Production of F(ab')$_2$ Fragments:

16 mg (100 nanomoles) of the antibody 7B10D11 is dissolved in 1 ml of a mixture of 0.1-molar acetate buffer (pH 4.5) and 0.1-molar sodium chloride solution and, after adding 0.3 mg of pepsin, is incubated for 20 hours at 37° C. After purification over "Ultragel" AcA 44 (company: LKB) at pH 7.0 and after freeze-drying, 6.3 mg (63% of theory) of the desired fragments is obtained.

(b) Production and Coupling of Fab Fragments:

15 mg (150 nmol) of the fragments obtained according to (a) is dissolved in 14.5 ml of 0.1-molar phosphate buffer (pH 6.0) and dissolved with 0.15 ml of a 0.1-molar mercaptoethylamine solution in 0.1-molar phosphate buffer (pH 6.0) with the addition of 15 mmol of ethylenediaminetetraacetic acid. After 2 hours of incubating at 37° C., the mixture is separated under a protective argon blanket over a "Sephadex" G 25 column. Determination of the sulfhydryl groups yields 238 nmol of SH-groups in the reaction batch.

0.7 mg (2.15 µmol) of the complexing agent described in Example 9j is dissolved in 10 ml of 0.1-molar phosphate buffer (pH 6.0). The above-prepared solution of the Fab fragment is added thereto at 4° C. and the mixture is allowed to react overnight with slight shaking (at maximally 4° C.). Thereafter the mixture is eluted over a cation exchanger, dialyzed against 0.1-molar ammonium acetate solution, and lyophilized, thus obtaining 14.1 mg of a white powder.

1 ml of $^{111}InCl_3$ solution (pH 5.5, 83 mCi/ml) is added to a solution of the conjugate in 25 ml of buffer (20 mmol, sodium acetate; 150 mmol, sodium chloride) and incubated for 4 hours. Thereafter another 5 ml of 0.1-molar sodium acetate solution is added, the mixture is dialyzed and lyophilized, and the product is 13.82 mg of a white powder having a specific activity of 5 mCi/mg.

EXAMPLE 36

$^{111}$Indium Complex of the Conjugate of the Monoclonal Antibody 7B10D11 with 15-[4-[4-Aza-2,6-diamino-N,N,N',N'',N''-pentakis(carboxymethyl) hexyl]phenoxy]-12-aza-14-hydroxypentadecanoic Acid Hydrazide 30 nmol of the antibody is bound to a macroporous, strongly acidic cation exchanger previously equilibrated with a 0.1-molar sodium acetate buffer (pH 5) and present in a column protected from incident light by an aluminum foil. Then the mixture is flushed with 0.03-molar sodium periodate in acetate buffer until the periodate appears in the eluate. Flushing is interrupted for 30 minutes, then the mixture is washed with acetate buffer and thereafter a solution is applied 0.03-molar with respect to the above hydrazide (Example 32) and 0.1-molar with respect to sodium cyanoborohydride. After 2 hours, complexing agent that has not entered into the coupling reaction is eluted with acetate buffer; the conjugate is eluted with a sodium chloride gradient. After desalting, the mixture is freeze-dried, thus obtaining 4.5 mg of conjugate which is converted into the 111indium complex as described in Example 35.

EXAMPLE 37

(a) N-Carbobenzoxyserin (2-carbobenzoxyaminoethylen) amide 7.34 g (30.7 mmol) of N-carbobenzoxyserine is reacted in accordance with the directions given in Example 9b with the corresponding amounts of chloroformic acid ethyl ester, triethylamine and N-(2-aminoethyl)carbamic acid benzyl ester hydrochloride, and worked up, thus obtaining 10.33 g (81%) of a colorless crystallized product.

Melting point: 167° C.
Analysis
Calcd: C 60.71; H 6.06; N 10.11; O 23.1.
Found: C 60.75; H 5.98; N 10.15.

(b)(2-Aminoethyl) serinamide 13.46 g of N-carbobenzoxyserin(2-carbobenzoxyaminoethylen)amide is hydrogeanted in 200 ml of methanol in the presence of 1.37 g of 10% palladium-carbon until hydrogen is no longer absorbed. The mixture is filtered off from the catalyst and all volatile components are removed by an oil pump. A viscous, partially crystalline oil remains.

Yield: 4.67 g (98%)
Analysis
Calcd: C 40.80; H 8.89; N 28.55; O 21.74.
Found: C 40.71; H 8.85; N 28.30.

(c) 1-Hydroxymethyl-1,3,5-triazapentane Trihydrochloride

Analogously to the directions for Example 9e, the title compound is obtained in a 67% yield from the aforedescribed amide as a white crystalline powder.

Melting point: 236° C. (decomposition)
Analysis
Calcd: C 24.75; H 7.47; N 17.32; O 6.59; Cl 43.84.
Found: C 24.71; H 7.40; N 17.41; Cl 43.98.

(d) 4-Hydroxymethyl-3,6,9-triaza-3,6,9-tris(tert-butoxycarbonylmethyl)undecanoic Acid Di-tert-butyl-diester The title compound is obtained in a 78% yield as a colorless oil analogously to the directions for Example 1a (after chromatography on silica gel with ether/hexane=½).

Analysis
Calcd: C 59.71; H 9.31; N 5.97; O 25.0.
Found: C 59.66; H 9.32; N 5.99.

(e) The gadolinium complex and, respectively, its salts are obtained as described in Example 1e.

Gadolinium Complex
Analysis
Calcd: C 42.55; H 5.95; N 9.92; O 41.56.
Found: C 43.08; H 5.88; N 9.73.

Sodium Salt of the Gadolinium Complex
Analysis
Calcd: C 30.04; H 3.53; N 7.00; O 29.35; Gd 26.22; Na 3.83.
Found: C 30.51; H 3.55; N 7.04; Gd 26.22; Na 3.88.

N-Methylglucamine Salt of the Gadolinium Complex
Analysis
Calcd: C 31.19; H 3.83; N 7.27; O 30.46; Gd 27.22.
Found: C 31.70; H 3.84; N 7.21; Gd 27.36.

EXAMPLE 38

(a) Bis-1,4-[4-[2,6-di[bis(tert-butoxycarbonylmethyl)amino]-4-(tert-butoxycarbonylmethyl)azahexamethylene]phenoxy] butane 13.7 g (17.56 mmol) of 4-(4-hydroxybenzyl)-3,6,9-triaza-3,6,9-tris(tert-butoxycarbonylmethyl)undecanedioic acid bis (tert-butyl)diester (Example 9f) is dissolved in dry toluene (100 ml), gently combined with 530 mg (17.6 mmol) of NaH (80% suspension in paraffin), and heated for 10 minutes to 40°–50° C. Thereafter the mixture is cooled to 0° C. and combined with 1.9 g (8.8 mmol) of dibromobutane in 10 ml of toluene. The mixture is allowed to warm up to room temperature and then heated for another 30 minutes to 80°–100° C. After filtration over glass wool and evaporation of the solvent, the mixture is chromatographed on silica gel, thus obtaining 10.5 g (6.5 mmol, 74% of theory) of a colorless oil.

Analysis
Calcd: C 63.99; H 8.99; N 5.2; O 21.8.
Found: C 64.57; H 9.11; N 5.18.

(b) Bis-1,4-[4-[2,6-di[bis(carboxymethyl)amino]-4-(carboxymethyl)azahexamethylene]phenoxy]butane As described for Example 1e, the free complexing agent is obtained in a 73% yield in the form of white crystals, melting point 228° C. (decomposition).

Analysis
Calcd: C 52.46; H 6.12; N 7.98; O 33.42.
Found: C 52.1; H 6.12; N 8.05.

The gadolinium complex, as well as its salts, are obtained quantitatively as described in Example 1e.

Gd Complex
Analysis
Calcd: C 40.58; H 4.29; N 6.17; O 25.85; Gd 32.09.
Found: C 40.21; H 4.32; N 6.18; Gd 23.32.

Sodium Salt of the Gd Complex
Analysis
Calcd: C 39.31; H 4.01; N 5.97; O 25.04; Na 3.27; Gd 22.37.
Found: C 38.91; H 3.94; N 6.08; Na 3.31; Gd 22.11.

N-Methylglucamine Salt of the Gd Complex
Analysis
Calcd: C 41.48; H 5.92; N 6.53; O 31.36; Gd 14.68.
Found: C 42.27; H 5.84; N 6.47; Gd 14.62.

EXAMPLE 39

(a) N,N'-Bis[4-[3-(tert-butoxycarbonylmethyl)aza-5-bis(tert-butoxycarbonylmethyl)amino-2-bis(tert-butoxycarbonylmethyl)aminomethyl]pentamethylenephenoxyacetyl]hydrazide A solution of 4.18 g (4.99 mmol) of 5-[4-(carboxymethoxy)benzyl]-3,6,9-triaza-3,6,9-tris(tert-butoxycarbonylmethyl)undecanedioic acid bis(tert-butyl) diester (Example 24a) and equimolar amounts of triethylamine and chloroformic acid isobutyl ester, prepared in 250 ml of tetrahydrofuran at 0° C. under exclusion of moisture, is gradually combined with further cooling with a solution of 74 mg (2.49 mmol) of hydrazine in 50 ml of tetrahydrofuran. After one hour of stirring at 5° C., another hour at room temperature, and 30 minutes at 45° C., the mixture is cooled, concentrated, and taken up in ethyl acetate. After filtering, the mixture is repeatedly washed with water and 0.1N hydrochloric acid. Finally, the product is chromatographed on silica gel with ether/hexane, thus obtaining 3.17 g (76% of theory) of a colorless oil.

Analysis
Calcd: C 61.77; H 8.55; N 6.7; O 22.96.
Found: C 62.26; H 8.52; N 6.61.

(b) N,N'-Bis [4-[3-(carboxymethyl)aza-5-bis(carboxymethyl)amino-2-bis(carboxymethyl)aminomethyl]pentamethylenephenoxyacetyl] hydrazide The free complexing agent is obtained in accordance with the procedure outlined in Example 1e in a 78% yield as a white powder, melting point 205° C. (decomposition).

Analysis
Calcd: C 49.72; H 5.62; N 10.08; O 34.56.
Found: C 49.77; H 5.67; N 10.03.

The gadolinium complex, as well as its salts, are obtained quantitatively as described in Example 1e.

Gd Complex
Analysis
Calcd: C 38.92; H 3.97; N 7.89; O 27.05; Gd 22.15.
Found: C 38.71; H 3.91; N 7.87; Gd 22.34.

Sodium Salt of the Gd Complex
Analysis
Calcd: C 37.75; H 3.71; N 7.65; O 26.23; Na 3.14; Gd 21.49.
Found: C 37.82; H 3.70; N 7.72; Na 3.09; Gd 21.13.

N-Methylglucamine Salt of the Gd Complex
Analysis
Calcd: C 40.39; H 5.68; N 7.63; O 31.99; Gd 14.29.
Found: C 40.56; H 5.70; N 7.54; Gd 14.13.

EXAMPLE 40

(a) 1,12-Bis-[4-[3-(tert-butoxycarbonylmethyl) aza-5-bis(tert-butoxycarbonylmethyl)amino-2-bis(tert-butoxycarbonylmethyl)aminomethyl]pentamethylenephenoxy]-4,9-diaza-5,8-dioxododecamethylene At 0° C., 770 mg (4.96 mmol) of succinic acid dichloride is gently added dropwise to 8.36 g (9.99 mmol) of 5-[4-(3-aminopropoxy)benzyl]-3,6,9-tris(tert-butoxycarbonylmethyl)-3,6,9-triazaundecanedioic acid bis(tert-butyl)diester (Example 18b) in 100 ml of toluene and an equimolar amount of triethylamine. Then the mixture is heated briefly to reflux, filtered, the organic phase thoroughly washed with water, and chromatographed on silica gel. Finally, 7.62 g (82% of theory) of a colorless oil is obtained.

Analysis
Calcd: C 62.92; H 9.05; N 7.48; O 20.52.
Found: C 61.63; H 8.95; N 7.56.

(b) 1,12-Bis[4-[3-(carboxymethylaza)-5-bis (carboxymethyl)amino-2-bis(carboxymethyl) aminomethyl]pentamethylenephenoxy]-4,9-diaza-5,8-dioxododecamethylene As described for Example 1e, the free complexing agent is obtained in a 78% yield.

Melting point: 220° C. (decomposition).

Analysis
Calcd: C 53.20; H 6.77; N 10.69; O 29.32.
Found: C 52.82; H 6.80; N 10.76.

The gadolinium complex, as well as its salts, are obtained quantitatively as described in Example 1e.

Gd Complex
Analysis
Calcd: C 43.05; H 5.1; N 8.65; O 23.72; Gd 19.43.
Found: C 43.28; H 5.1; N 8.74; Gd 19.51.

Sodium Salt of the Gd Complex
Analysis
Calcd: C 41.92; H 4.85; N 8.42; O 23.10; Na 2.76; Gd 18.92.
Found: C 42.63; H 4.81; N 8.28; Na 2.71; Gd 18.57.

N-Methylglucamine Salt of the Gd Complex
Analysis
Calcd: C 43.06; H 6.30; N 8.17; O 29.34; Gd 13.11.
Found: C 43.91; H 6.19; N 8.29; Gd 13.06.

EXAMPLE 41

(a) 3,6-Diaza-3,6-bis(tert-butoxycarbonylmethyl)-4-[4-(3-[5-[2-oxo-2,3,3a,4,6,6a-hexahydro-1H-thieno[3,4-d]imidazol-4-yl]valerylamino]propoxy)benzyl] suberic Acid Bis(tert-butyl)diester 341.4 mg (1 mmol) of N-hydroxysuccinimidobiotin (Pierce Chem. Comp.) is combined with 679.9 mg (1 mmol)

of 3,6-diaza-3,6-bis(tert-butoxycarbonylmethyl)-4-[4-(3-aminopropoxy)benzyl]suberic acid bis(tert-butyl)diester (Example 1c) in 6 ml of DMF and stirred overnight. Then the reaction solution is concentrated by evaporation and chromatographed on silica gel (toluene/glacial acetic acid/ethyl acetate/methanol=6:4:4:3). The fractions, purified by thinlayer chromatography, are combined, the solution is evaporated under vacuum, and dried over KOH. Yield: 695 mg (78% of theory).

Analysis
Calcd: C 60.97; H 8.34; N 7.73; O 19.42; S 3.54.
Found: C 61.05; H 8.29; N 7.71; S 3.30.

(b) 3,6-Diaza-3,6-bis(carboxymethyl)-4-[4-(3-[5-[2-oxo-2,3,3a,4,6,6a-hexahydro-1H-thieno[3,4-d]imidazol-4-yl]valerylamino]propoxy)benzyl]suberic Acid 453 mg (0.5 mmol) of compound 41a is combined with 3 ml of trifluoroacetic acid and stirred for 30 minutes. The mixture is then precipitated with dry diethyl ether, the precipitate is washed with diethyl ether, and dried. Yield: 298 mg (90% of theory).

Analysis
Calcd: C 52.85; H 6.40; N 10.27; O 25.81; S 4.70.
Found: C 52.79; H 6.49; N 10.20; S 4.59.

The gadolinium complex is prepared according to the procedure described in Example 1e.

Analysis
Calcd: C 43.10; H 4.82; N 8.38; O 21.05; S 3.84; Gd 18.81.
Found: C 43.01; H 4.79; N 8.45; S 3.97; Gd 18.47.

EXAMPLE 42

(a) 3,6,9-Triaza-4-(4-hydroxybenzyl)-3,6,9-tris(carboxymethyl)undecanedioic Acid 7.80 g (10 mmol) of 3,6,9-triaza-4-(4-hydroxybenzyl)-3,6,9-tris(tert-butoxycarbonylmethyl)undecanedioic acid bis(tert-butyl)diester (Example 9f) is dissolved in 100 ml of trifluoroacetic acid and, after one hour, precipitated with diethyl ether. After chromatoggraphy on silica gel in ethanol/concentrated ammonia/water (8:1:1), the purified fractions are passed over "Amberlite" IR 120 (H$^+$), and the acidic eluate is freeze-dried. Yield: 4.09 g (82% of theory).

Analysis
Calcd: C 50.50; H 5.85; N 8.41; O 35.24.
Found: C 50.39; H 5.85; N 8.34.

(b) Gadolinium Complex of 3,6,9-Triaza-4-(4-hydroxybenzyl)-3,6,9-tris(carboxymethyl)undecanedioic Acid 0.50 g (1 mmol) of the complex acid disclosed in Example 42a is dissolved in 40 ml of water and combined with 181 mg (0.5 mmol) of Gd$_2$O$_3$, stirred for 30 minutes at 80° C., filtered, and the filtrate is freeze-dried.

Yield: 0.65 g (99.4% of theory).

Analysis
Calcd: C 38.58; H 4.01; N 6.43; O 26.92; Gd 24.06.
Found: C 38.39; H 4.02; N 6.47; Gd 24.11.

EXAMPLE 43 a) Bis-1,10-{4-[2,6-di(bis-t-butoxycarbonylmethylamino)-4-(t-butoxycarbonylmethyl)-4-azahexamethylene]-phenoxy}decane 9.36 g (12 mmol) of 4-(4-hydroxybenzyl)-3,6,9-triaza-3,6,9-tris(tert-butoxycarbonylmethyl)undecanedioic acid-bis-(tert-butyl)diester (Example 9f) is dissolved in dimethylformamide (100 ml), mixed with 0.40 g (13.2 mmol) of sodium hydride (80% in paraffin, and, after adding 1.80 g (6 mmol) of 1,10-bis-bromodecane, it is stirred overnight at 80° C. The solvent is concentrated by evaporation in a vacuum, and the residue is chromatographed on silica gel (ether/hexane/triethylamine 12:8:1). 5.6 g (55% of theory) of a colorless oil is obtained.

Elementary analysis:

Cld: C 65.07; H 9.26; N 4.95.

Fnd: C 64.82; H 9.48; N 5.06.

b) Digadolinium complex of bis-1,10-{4-[2,6-di(bis-carboxymethylamino)-4-(carboxymethyl)-4-azahexamethylene]phenoxy}-decane, tetrasodium salt 5.09 g (3 mmol) of the deca-tert-butyl ester described in Example 43a is dissolved in methanol and mixed with 5.4 ml of 10N sodium hydroxide solution (54 mmol) and refluxed for 2 hours. After cooling the solution, methanol is concentrated by evaporation in a vacuum, water is added, and it is adjusted to pH 3 with Amberlite IR 120® (H$^+$form), mixed with 1.09 g (3 mmol) of Gd$_2$O$_3$ and complexed for 2 hours at 80°. The solution, cooled to room temperature, is adjusted to pH 7 by adding diluted sodium hydroxide solution. The solution is freeze-dried. 4.89 g of colorless lyophilizate is obtained.

Yield: 98.4% of theory

Water content (Karl Fischer): 7.5%

Gd content (AAS): 19.3%

Elementary analysis (relative to anhydrous substance):

Cld: C 40.37; H 4.34; Gd 20.51; N 5.48; Na 6.00.

Fnd: C 40.49; H 4.61; Gd 20.17; N 5.62; Na 5.84.

EXAMPLE FOR NMR DIAGNOSTICS IN VIVO

Imaging of Gallbladder and a Colon Carcinoma by NMR Tomograph

A hairless mouse (Balb/c nu/nu, female, 20 g) with subcutaneously implanted HT29 colon carcinoma received intravenously 0.1 mmol/kg of the gadolinium complex of 3,6,9-triaza-4-(4-hydroxybenzyl)-3,6,9-tris(carboxymethyl)undecanedioic acid (Example dissolved in 200 µl of physiological phosphate buffer.

Images were produced prior to and after administration of the contrast medium with a spin echo sequence (T$_R$=400 msec, T$^E$=30 msec) in the region of the liver and the tumor. The studies were performed with a 2 tesla NMR tomograph of the company General Electric.

The scan shows three photographs: one prior to and two after administration of the contrast medium. The gallbladder, 30 minutes after administration, is clearly distinguishable from the surrounding liver tissue. The tumor exhibits immediately after administration signal amplification in the marginal zone whereas a marked signal enhancement can be perceived after 30 minutes in the entire tumor.

What is claimed is:

1. A compound of general formula I

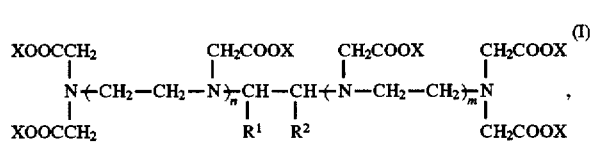

wherein n and m in each case are the numbers 0, 1, 2, 3, and 4;

X stands for a hydrogen atom and/or a metal ion equivalent of an element of atomic numbers 21–29, 42, 44 of 57–83;

$R^1$ and $R^2$, being different, are in each case a hydrogen atom or a straight-chain, branched, or cyclic, saturated or unsaturated $C_1$–$C_{20}$-alkylene group, said alkylene group optionally containing imino, phenylenoxy, phenylenimino, amido, hydrazido, ester group(s), oxygen, sulfur and/or nitrogen atom(s) and is optionally substituted by hydroxy, mercapto, imino, epoxy, oxo, thioxo and/or amino group(s), said alkylene group exhibiting at the end either a moiety of general formula $I_A$ or $I_B$

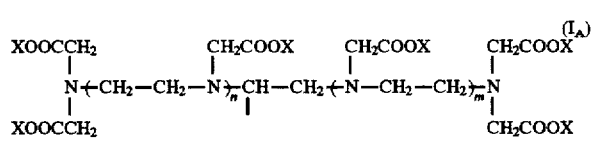

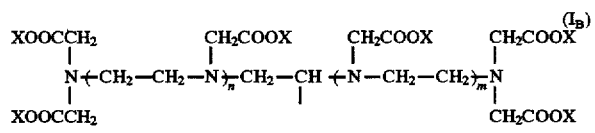

wherein at least one of $R^1$ and $R^2$ is said alkylene group having at the end thereof a moiety of formula $I_A$ or formula $I_B$;

with the proviso that n and m jointly result in 1–4 and that at least two of the substituents X mean a nonradioactive metal ion equivalent; or a salt thereof with at least one inorganic and/or organic base or amino acid.

2. A method for enhancing a magnetic resonance image comprising administering to a patient a pharmaceutical composition comprising:

(a) an effective amount of a compound of the formula I

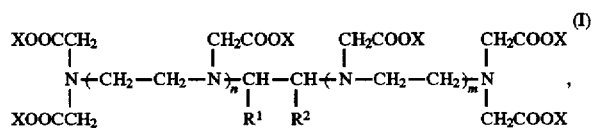

wherein n and m in each case are, independently, 0, 1, 2, 3 or 4;

X in each case is a hydrogen atom and/or a metal ion equivalent of an element of atomic numbers 21–29, 42, 44 or 58–70;

$R^1$ and $R^2$ are different and mean, in each case, a hydrogen atom or a straight-chain, branched, or cyclic, saturated or unsaturated $C_{1-20}$-alkylene group which optionally contains imino, phenylenoxy, phenylenimino, amido, hydrazido, ester group(s), oxygen, sulfur and/or nitrogen atom(s) and is optionally substituted by hydroxy, mercapto, imino, epoxy, oxo, thioxo and/or amino group(s), said alkylene group having at the end a second group of formula $I_A$ or $I_B$

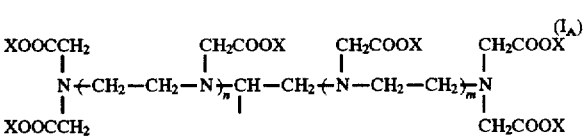

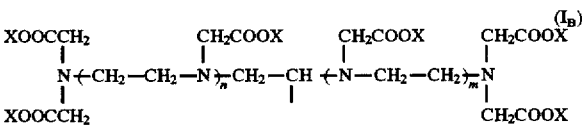

with the provisos that n+m, in each case, is 1–4, and at least two of the substituents X are said metal ion equivalent; or a salt thereof with an inorganic and/or organic base or amino acid; and (b) a pharmaceutically acceptable carrier.

3. A method of enhancing an X-ray image comprising administering to a patient a pharmaceutical composition comprising:

(a) an effective amount of a compound of the formula I

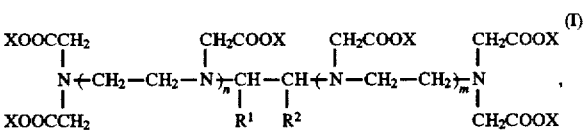

wherein n and m in each case are, independently, 0, 1, 2, 3 or 4;

X in each case is a hydrogen atom and/or a metal ion equivalent of an element of atomic numbers 21–29, 42, 44 or 57–83;

$R^1$ and $R^2$ are different and mean, in each case, a hydrogen atom or a straight-chain, branched, or cyclic, saturated or unsaturated $C_{1-20}$-alkylene group which optionally contains imino, phenylenoxy, phenylenimino, amido, hydrazido, ester group(s), oxygen, sulfur and/or nitrogen atom(s) and is optionally substituted by hydroxy, mercapto, imino, epoxy, oxo, thioxo and/or amino group(s), said alkylene group having at the end a second group of formula $I_A$ or $I_B$

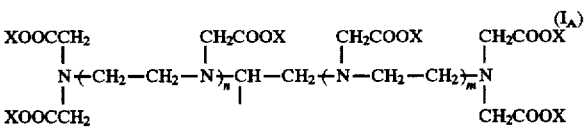

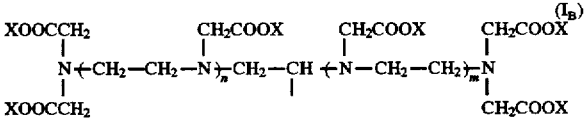

with the provisos that n+m, in each case, is 1–4, and at least two of the substituents X are said metal ion equivalent; or a salt thereof with an inorganic and/or organic base or amino acid; and (b) a pharmaceutically acceptable carrier.

4. A compound according to claim 1, wherein n in each case is 0, m in each case is 1 and $R^2$ is H.

5. A compound according to claim 4, wherein $R^1$ exhibits at its end a moiety of formula $I_a$.

6. A compound according to claim 4, wherein $R^1$ exhibits at its end a moiety of formula $I_b$.

7. A compound according to claim 1, wherein n in each case is 0, m in each case is 1 and $R^1$ is H.

8. A compound according to claim 7, wherein $R^2$ exhibits at its end a moiety of formula $I_a$.

9. A compound according to claim 7, wherein $R^2$ exhibits at its end a moiety of formula $I_b$.

10. A compound according to claim 1, wherein said alkylene group contains one or more phenoxy groups.

11. A compound according to claim 1, wherein said alkylene groups contains one or more phenylenimino groups.

12. A compound according to claim 1, wherein said alkylene group is a straight-chain or branched, saturated or unsaturated $C_{1-20}$-alkylene group optionally containing imino group(s), amido group(s), hydrazido group(s), ester group(s), oxygen atom(s), sulfur atom(s) and/or nitrogen atom(s) and is optionally substituted by hydroxy, mercapto, imino, epoxy, oxo, thioxo and/or amino group(s).

13. A compound according to claim 1, wherein said alkylene group contains a cyclic saturated structure.

14. A compound according to claim 1, wherein said alkylene group contains a cyclic unsaturated structure.

15. A method according to claim 2, wherein said compound is a gadolinium complex of bis-1,4-[4-[2,6-di[bis(carboxymethyl)amino]-4-(carboxymethyl)azahexamethylene]phenoxy]butane.

16. A method according to claim 2, wherein said compound is a gadolinium complex of N,N'-bis[4-[3-(carboxymethyl)aza-5-bis(carboxymethyl)amino-2-bis(carboxymethyl)aminomethyl]pentamethylenephenoxyacetyl]hydrazide.

17. A method according to claim 2, wherein said compound is a gadolinium complex of 1,12-bis[4-[3-(carboxymethylaza)-5-bis(carboxymethyl)amino-2-bis(carboxymethyl)aminomethyl]pentamethylenephenoxy]-4,9-diaza-5,8-dioxododecamethylene.

18. A compound according to claim 1, wherein said compound is a digadolinium complex of bis-1,10-{4-[2,6-di(bis-carboxymethylamino)-4-(carboxymethyl)-4-azahexamethylene]-phenoxy}decane.

19. A method according to claim 3, wherein said compound is a gadolinium complex of bis-1,4-[4-[2,6-di[bis(carboxymethyl)amino]-4-(carboxymethyl)azahexamethylene]phenoxy]butane.

20. A method according to claim 3, wherein said compound is a gadolinium complex of N,N'-bis[4-[3-(carboxymethyl)aza-5-bis(carboxymethyl)amino-2bis(carboxymethyl)aminomethyl]pentamethylenephenoxyacetyl]hydrazide.

21. A method according to claim 3, wherein said compound is a gadolinium complex of 1,12-bis[4-[3-(carboxymethylaza)-5-bis(carboxymethyl)amino-2-bis(carboxymethyl)aminomethyl]pentamethylenephenoxy]-4,9-diaza-5,8-dioxododecamethylene.

22. A method according to claim 2, wherein said compound is a digadolinium complex of bis-1,10-{4-[2,6-di(bis-carboxymethylamino)-4-(carboxymethyl)-4-azahexamethylene]-phenoxy}-decane.

23. A method according to claim 3, wherein said compound is a digadolinium complex of bis-1,10-{4-[2,6-di(bis-carboxymethylamino)-4-(carboxymethyl)-4-azahexamethylene]-phenoxy}-decane.

24. A pharmaceutical composition comprising a compound according to claim 1 and a pharmaceutical carrier.

25. A composition according to claim 24, wherein said compound is a gadolinium complex of bis-1,4-[4-[2,6-di[bis(carboxymethyl)amino]-4-(carboxymethyl)azahexamethylene]phenoxy]butane.

26. A composition according to claim 24, wherein said compound is a gadolinium complex of N,N'-bis[4-[3-(carboxymethyl)aza-5-bis(carboxymethyl)amino-2-bis(carboxymethyl)aminomethyl]pentamethylenephenoxyacetyl]hydrazide.

27. A composition according to claim 24, wherein said compound is a gadolinium complex of 1,12-bis[4-[3-(carboxymethylaza)-5-bis(carboxymethyl)amino-2-bis(carboxymethyl)aminomethyl]pentamethylenephenoxy]-4,9-diaza-5,8-dioxododecamethylene.

28. A composition according to claim 24, wherein said compound is a digadolinium complex of bis-1,10-{4-[2,6-di(bis-carboxymethylamino)-4-(carboxymethyl)-4-azahexamethylene]-phenoxy}-decane.

* * * * *